(12) United States Patent
Chen et al.

(10) Patent No.: US 8,799,030 B1
(45) Date of Patent: Aug. 5, 2014

(54) METHODS AND SYSTEMS FOR DISEASE MANAGEMENT CARE COORDINATION

(75) Inventors: Michael Z. Chen, St. Louis, MO (US); Ann Hilstrom, Saint Peters, MO (US); Anthony L. Grillo, High Ridge, MO (US)

(73) Assignee: Express Scripts, Inc., St. Louis, MO (US)

( * ) Notice: Subject to any disclaimer, the term of this patent is extended or adjusted under 35 U.S.C. 154(b) by 0 days.

(21) Appl. No.: 13/338,860

(22) Filed: Dec. 28, 2011

Related U.S. Application Data

(60) Provisional application No. 61/435,217, filed on Jan. 21, 2011.

(51) Int. Cl.
*G06F 19/00* (2011.01)
(52) U.S. Cl.
CPC .................................. *G06F 19/322* (2013.01)
USPC ............................................................ 705/4
(58) Field of Classification Search
CPC ..................................................... G06F 19/322
IPC ................................ G06Q 40/00; G06F 19/322
See application file for complete search history.

(56) References Cited

U.S. PATENT DOCUMENTS

| | | | |
|---|---|---|---|
| 7,325,076 B1 | 1/2008 | Morrison et al. | |
| 7,679,520 B2 | 3/2010 | Zerhusen et al. | |
| 8,073,708 B1* | 12/2011 | Igoe et al. | 705/2 |
| 2002/0044059 A1 | 4/2002 | Reeder et al. | |
| 2002/0196141 A1 | 12/2002 | Boone et al. | |
| 2004/0010425 A1 | 1/2004 | Wilkes et al. | |
| 2004/0176667 A1 | 9/2004 | Mihai et al. | |
| 2005/0055242 A1 | 3/2005 | Bello et al. | |
| 2007/0027722 A1 | 2/2007 | Hasan et al. | |
| 2007/0061393 A1* | 3/2007 | Moore | 709/201 |
| 2009/0265185 A1 | 10/2009 | Finn et al. | |
| 2010/0131299 A1 | 5/2010 | Hasan et al. | |
| 2012/0203565 A1* | 8/2012 | Hollin et al. | 705/2 |

* cited by examiner

*Primary Examiner* — Bruce I Ebersman
(74) *Attorney, Agent, or Firm* — Randy L. Canis, Esq.

(57) ABSTRACT

Methods and systems for disease management care coordination are described. In one embodiment, claim data associated with a prescription drug is integrated with additional health data from a plurality of data feeds received from a client device, a care coordination device, and a health management vendor device. The integrated data is targeted to identify a member. The integrated data associated with the member is transmitted to a patient evaluator device. The integrated data is updated using additional member information received from the patient evaluator device. Other methods and systems are described.

34 Claims, 16 Drawing Sheets

| Therapy Class | Possible Use | Drug | May | June | July | August |
|---|---|---|---|---|---|---|
| selective seratonin reputation | depression | Lexapro | 90** | | | |
| sulfonylureas | diabetes | Glimepiride | | 90** | | |
| sulfonylureas | diabetes | Glipizide | 180** | | | 180** |
| nitrates | heart disease | Isosorbide Dn | | 180** | | |
| hmg-COA reductase | high blood cholesterol | Lipitor | 30* | | 60* | 60* |
| antiadrenergic ant | high blood pressure/heart disease | Clonidine | 90** | | | 90** |
| Ace inhibitors | high blood pressure/heart disease | Lisinopril | 30* | 30* | | |
| Ace inhibitors | high blood pressure/heart disease | Lisinopril | | | | 60* |
| Diuredic combination | high blood pressure | Triam/HCTZ | 30* | 30* | | |
| Diuredic combination | high blood pressure | Triam/HCTZ | | | 90** | |
| Anticonvulsant | seizures | Gabapentin | 270** | 270** | | |
| Anti Opesity Agents | weight loss | Xenical | 90* | 90* | 90* | 90* |
| | | | | | | |
| Maintenance Drug Pill Burden(4 months) 13.25/day | | Total Qty/RX above. *=Retail, **=Mail | | | | |

FIG. 17

METHODS AND SYSTEMS FOR DISEASE MANAGEMENT CARE COORDINATION

RELATED APPLICATION

This disclosure claims priority to U.S. Provisional Patent Application No. 61/435,217, entitled "Methods and Systems for Disease Management Care Coordination," filed on Jan. 21, 2011, herein incorporated by reference in its entirety.

FIELD

The present disclosure generally relates to care coordination, and more particularly disease management care coordination.

BACKGROUND

It is not uncommon for more than one healthcare provider or vendor to provide healthcare to an individual. The many different entities may collect, utilize, and internally maintain information associated with a member to provide them with the appropriate care. Information about a member may include the medical history of the member, demographic information, medication history and allergies, and claims information. As the different vendors and providers may not even be aware that the member is receiving care from other vendors or providers, the various vendors and providers may each maintain records regarding the treatment of the individual, which may include partial or incomplete information.

BRIEF SUMMARY

Figure 13:
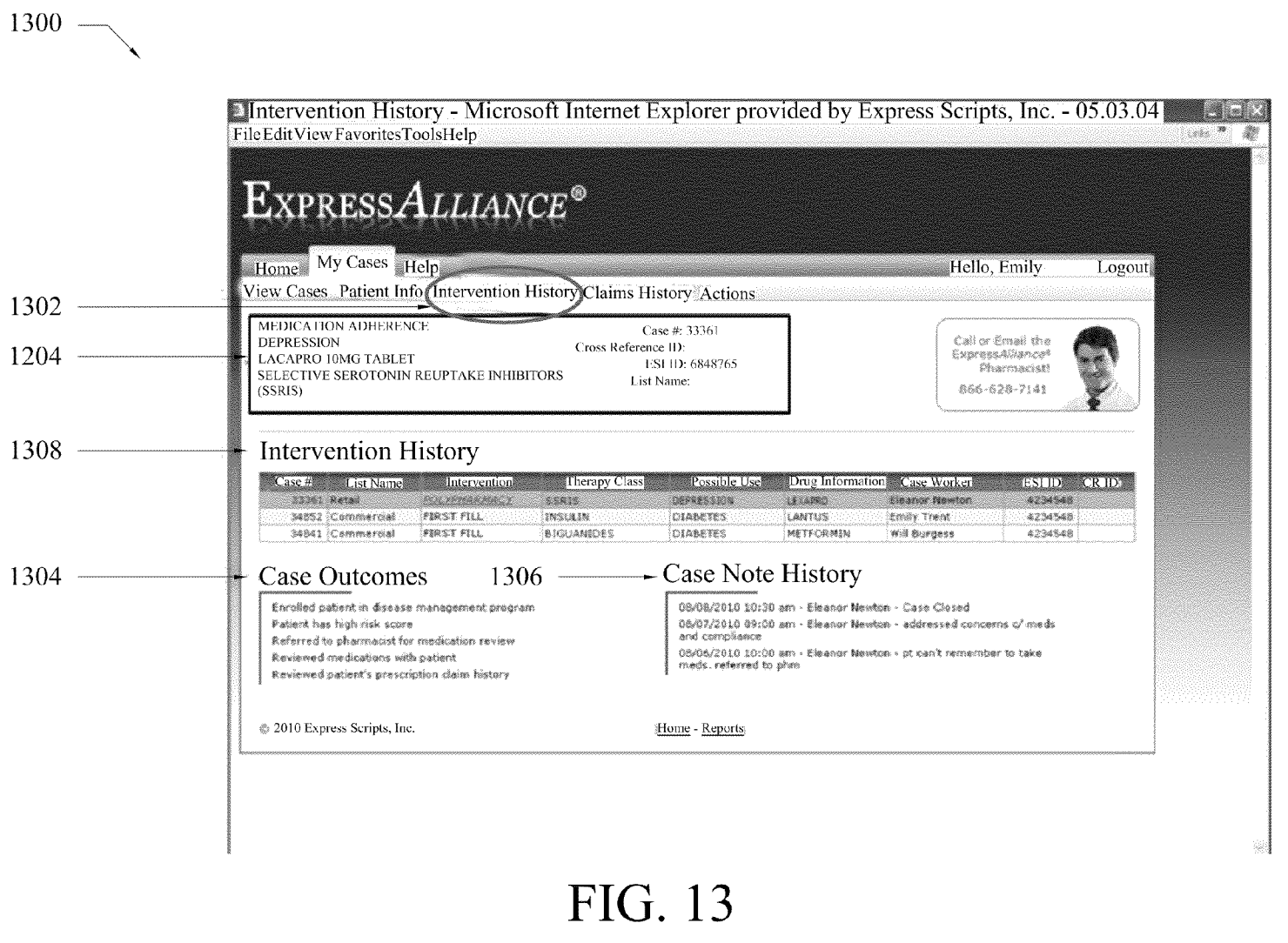
Figure 14:
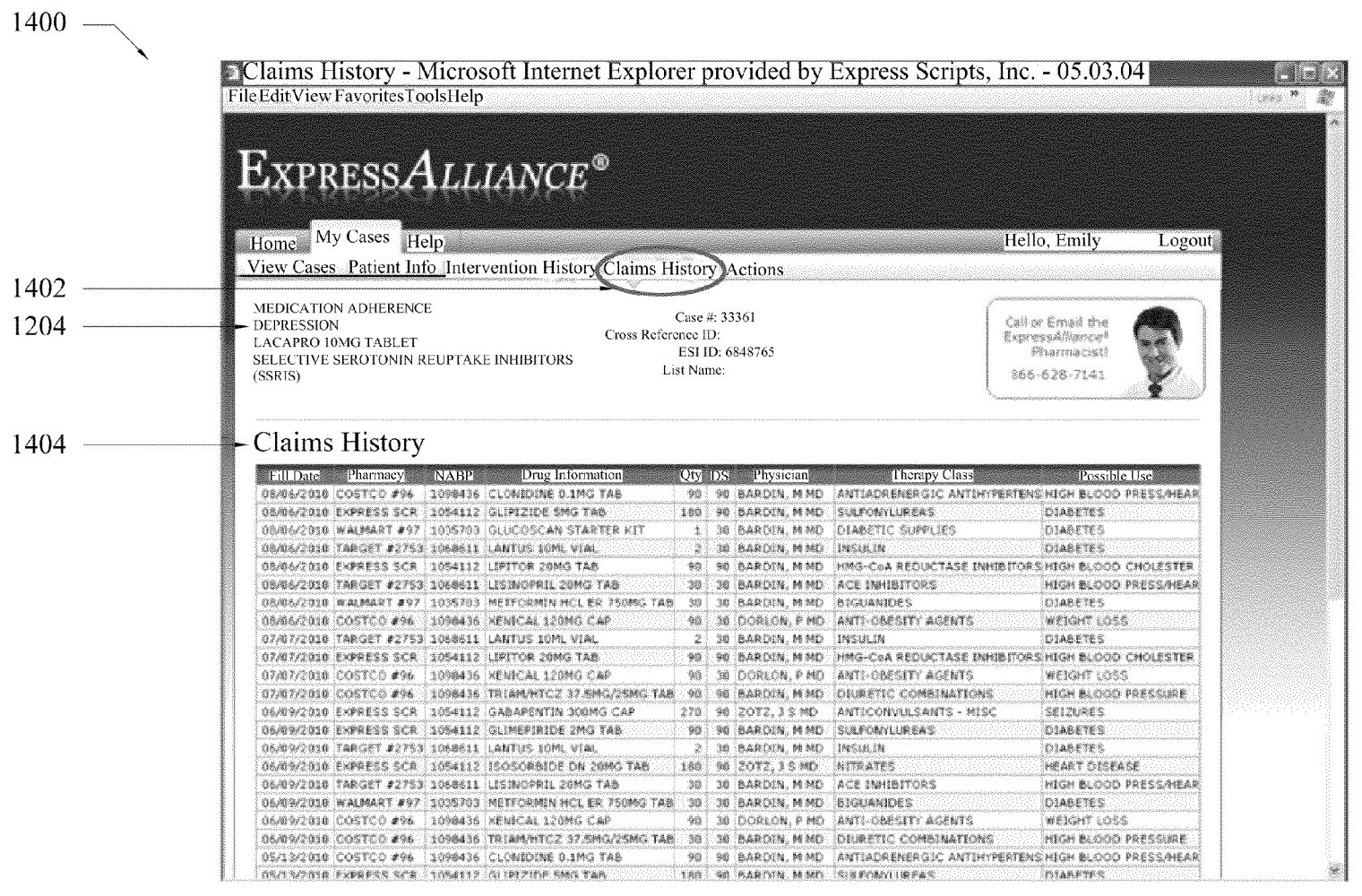
Figure 16:
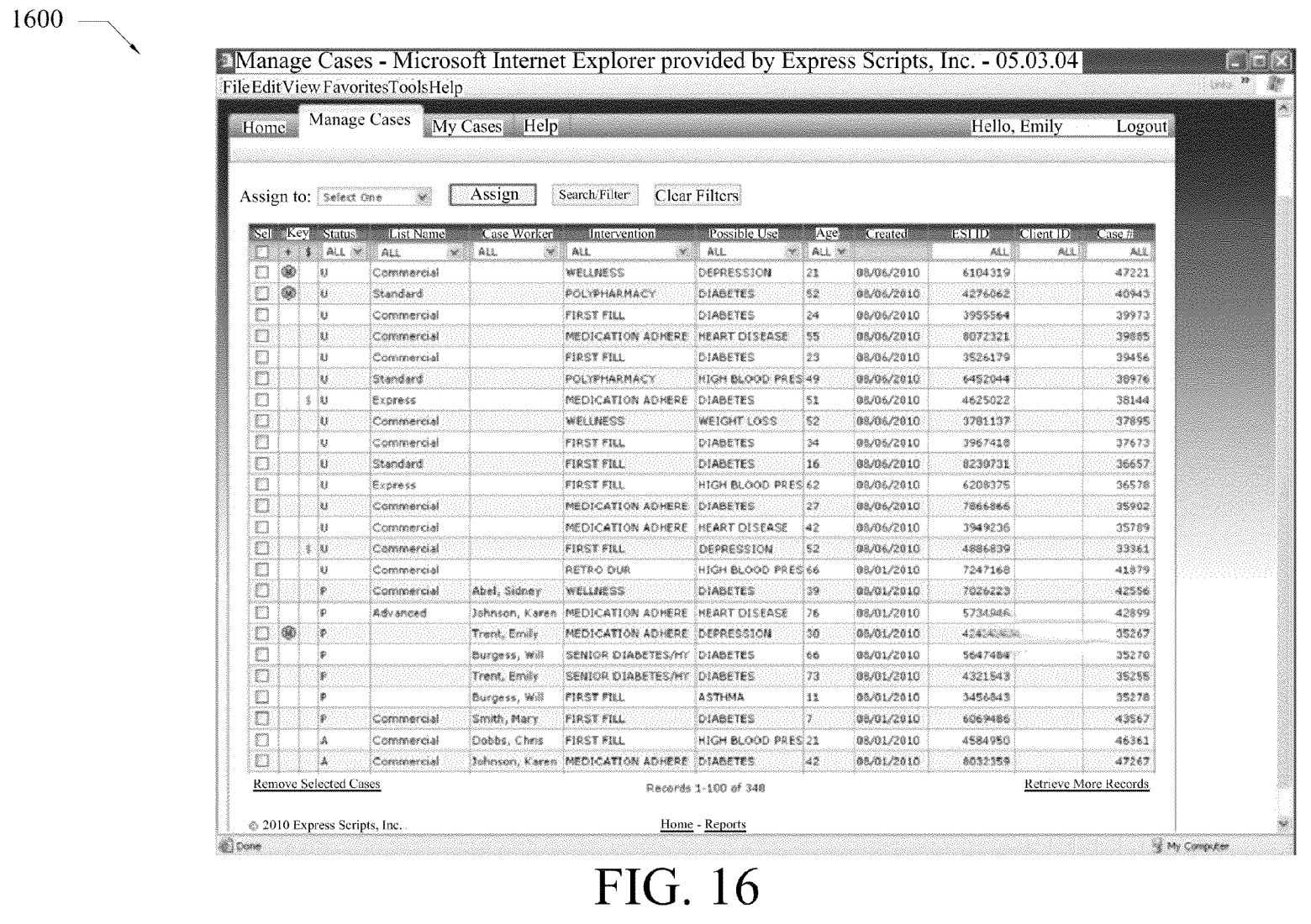

FIGS. 10-17 are example displays, according to example embodiments; and

DETAILED DESCRIPTION

Figure 1:
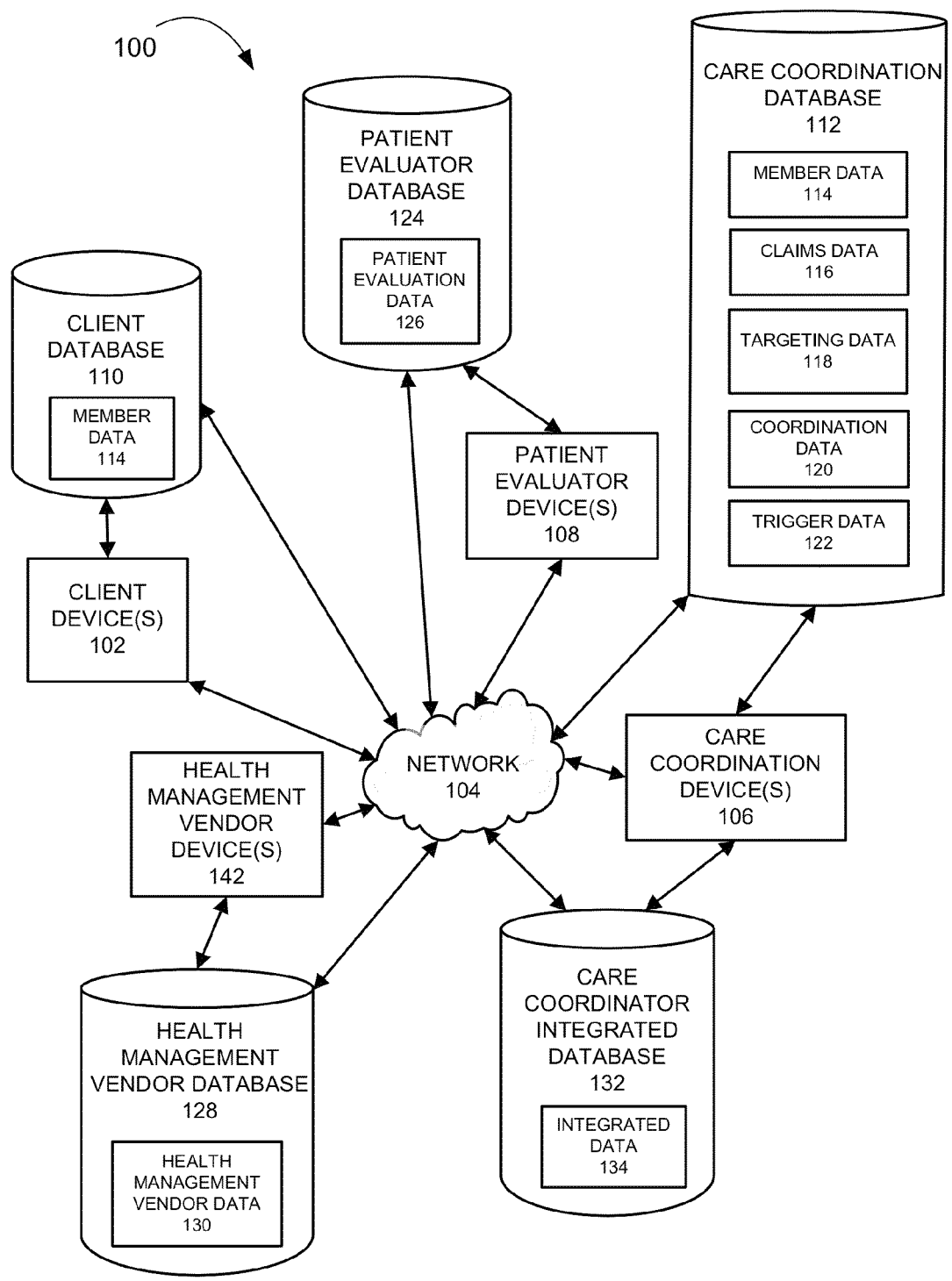
FIG. 1 is a block diagram of an example disease management care coordination system, according to an example embodiment.

Example methods and systems for disease management care coordination are described. In the following description, for purposes of explanation, numerous specific details are set forth in order to provide a thorough understanding of example embodiments. It will be evident, however, to one of ordinary skill in the art that embodiments of the invention may be practiced without these specific details.

In an embodiment, a disease management care coordination system may facilitate sharing information associated with members among different healthcare providers, care coordinators, and clients, which may allow a healthcare coordinator and its partners to work in a best practice environment. The targeting may include a number of queries that may be defined (e.g., by a clinician). Targeting may then be used to identify members according to different attributes. Attributes may include, but are not limited to, disease states, geographic location, medication received, type of health insurance, or other type of information associated with members.

The disease management care coordination system may reduce the barriers required to make better pharmacy intervention that may lead to better member outcomes. A care coordination system, according to an embodiment, may contain cases of a member population of a client generated by targeting by a healthcare coordinator. The system may provide access to the latest information available for members to target generated cases and pharmacy claims as well as the ability to document clinical intervention outcomes.

The methods and systems may be used to address fragmented care or the gap between the health care providers and vendors. A care coordinator may offer an integrated portfolio of services and tools to identify drug programs within a specific member population. Patient evaluators (e.g., nurses), may use the services and tools to identify members for outreach (e.g., members with problem cases), research the cases, obtain additional information from the care coordinator on the medications, and take action with the member in an attempt to improve the health of the member.

A disease management care coordination system may be used in a healthcare setting that provides a platform to integrate a healthcare coordinator with clients and vendors to improve member case management. The care coordination system may be a web-based system.

The disease management care coordination system may be used to organize information to enable providing of drug information and reviewing of member cases so that health management vendors can better utilize time making outreaches work.

In some embodiments, the methods and systems make prescription drugs safer and more affordable. In some embodiments, the use of the methods and system may reduce or eliminate the number of reports regarding cases of members provided by the care coordinator to a disease management group or client. In some embodiments, the methods and system may reduce the administrative burden of communicating with members regarding health issues. In some embodiments, the methods and systems may reduce duplicative communication of the members by both health care professionals and patient evaluators.

FIG. 1 is a block diagram of an example system 100, according to an example embodiment. The system 100 includes a client device 102 by which a client may communicate over a network 104 with a care coordination device 106, a patient evaluator device 108, and/or a health management vendor device 142.

Generally, a client engages a pharmacy benefit manager (PBM) to offer a drug benefit program. Examples of clients include governmental organizations (e.g., Federal government agencies, the Department of Defense, the Centers for Medicare and Medicaid Services and state government agencies), middle market companies, large national employers, health insurance companies that have carved out the drug benefit, and the like. The PBM may be a stand-alone PBM, or may be part of a larger organization that offers other benefits or services.

The client device 102 may be used by a client to maintain member information and receive reports from the care coordinator. The client may be an organization that engages the services of the care coordinator.

The client may be an employer group or health management vendor acting on behalf of the employer group (e.g., healthcare management vendor, such as a disease management vendor). Examples of employer groups include Boeing, Anheuser Busch Inbev, FedEx, and the like. An employer group may be a company, corporation, or similar entity that employs individuals but do not have the clinical abilities to provide healthcare for the individuals. The employer group may outsource clinical and other health care services for the group to another entity, such as a health management vendor (e.g., disease management vendor). Thus, the employer group hires patient evaluators to communicate with the members (e.g., employees) of the employer group regarding disease management. In some embodiments, the patient evaluators are associated with multiple health management vendors. The patient evaluators may be hired by (or otherwise work for) the employer group, or may be hired by the medical provider associated with the employer group. The healthcare coordinator may communicate with the one or more health management vendors on behalf of the client through vendor-to-vendor communications and may ensure that member issues, such as pharmacy issues, are addressed on behalf of the client.

The client may be a health plan that has its own patient evaluators or outsources the function of the patient evaluator. The health plan may provide medical services, pharmacy services, or both medical and pharmacy services. The health plan may have an internal or external source of patient evaluators. In some embodiments, health plans may not need to outsource the healthcare responsibilities to a health management vendor, but may be able to coordinate much of the healthcare needs internally.

A healthcare coordinator or care coordinator may be a vendor that facilitates communication between the various healthcare entities, such as the client, health management vendors, members, and other healthcare providers.

A health management vendor may be a vendor who receives claims data and review member claims to identify health improvement opportunities.

The reports received may document the success that the patient evaluators have had in working with the members of the client.

Examples of the network 104 by which the client device 102 may communicate with the care coordination device 106, the patient evaluator device 108, and/or health management vendor device 142 include Mobile Communications (GSM) network, a code division multiple access (CDMA) network, 3rd Generation Partnership Project (3GPP), an Internet Protocol (IP) network, a Wireless Application Protocol (WAP) network, a Wi-Fi network, or an IEEE 802.11 standards network, as well as various combinations thereof. Other conventional and/or later developed wired and wireless networks may also be used.

The care coordination device 106 may be used to access a disease management care coordination subsystem, discussed below. The care coordination device 106 is maintained by, or on behalf of, a care coordination organization.

The care coordinator coordinates care with the patient evaluators and the client (or entity acting on behalf of the client) to make sure that pharmacy issues of the members of the client are addressed.

The care coordinator and the patient evaluators may be in regular and/or periodic communication, but the ultimate results in the form of a report that may be provided to the client. The results may be provided to the client monthly, quarterly, annually, in real-time, or at other frequencies. In some embodiments, the results may reflect that the members are healthier as a result of the coordination of care between the care coordinator and the patient evaluators. When the client is a health management vendor (e.g., disease management group) acting on behalf of an employer group, the results may be provided to the health management vendor, the employer group, or both. An example of a company that provides care coordination services is Express Scripts, Inc. of St. Louis, Mo.

The patient evaluator device 108 is used by patient evaluators access a disease management care coordination subsystem, discussed below. The patient evaluators may use the computerized tool to provide better care and encourage healthy behavior among the members of the client.

The patient evaluators may be associated with a health management vendor (e.g., disease management group). For example, the employer group may hire a particular disease management group to talk to members of the employer group regarding disease management.

The health management vendor device 142 is used by health management vendors to access the disease management care coordination subsystem, discussed below, to maintain data about the members and coordinate care. The health management vendors may use the disease management care coordination subsystem, discussed below, to provide treatment to members and to communicate with healthcare partners, such as the clients, patient evaluators, and care coordinators, to gain a more comprehensive patient profile.

While patient evaluators may include nurses, other persons that may be patient evaluators include, but are not limited to, doctors and pharmacists. In some embodiments, the doctors and/or nurses may be associated with a clinic.

Examples of organizations that provide patient evaluators include CIGNA, Aetna, Anthem, and the like. The patient evaluators may also be internal to a health group. The patient evaluators may contact members for a variety of reasons including medical and/or pharmaceutical reasons.

The care coordinator may provide consultation (e.g., pharmaceutical consultation) to patient evaluators. The patient evaluators may use the received information when determining an action to take with respect to a member.

In some embodiments, the client device 102 and the patient evaluator device 108 are operated by a single entity. In other embodiments, the client device 102 and the patient evaluator device 108 are operated by different entities. In some embodiments, the client device 102 and the patient evaluator device 108 are combined into a single server. In some embodiments, the client device 102 and the patient evaluator device 108 operate on separate servers.

The disease management care coordination system may be implemented as a stand-alone device that solely provides at least some of the functionality to enable disease management care coordination, or may be a multi-use device that has functionality disease management care coordination as described herein. In some embodiments, the device may be a mobile device, a portable device, or a stationary computing device.

Examples of the devices 102, 106, 108, 146 include a gaming unit, a mobile phone, a personal digital assistant (PDA), a display device, a generic or specialized computing system, or the like. Other devices may also be used. The devices 102, 106, 108, 146 may each use the same type of device, or may use different types of devices.

The system 100 may further include a client database 110, a care coordinator database 112, a patient evaluator database 124, a health management vendor database 128, and/or a care coordinator integrated database 132.

The health management vendor device 142 may be in communication with a health management vendor database 128. The health management vendor database 128 may store health management vendor data 130. Health management vendor data 130 may include pharmacy claims data 116 and medical claims data 116 that may be used to identify health improvement opportunities.

The client device 102 may be in communication with a client database 110. The client database 110 may store member data 114 of the members of the client. Member data 114 may include demographic data, contact information, health insurance data, and other types of personal data associated with members.

The care coordination device 106 may be in communication with a care coordination database 112. The care coordination database 112 may store data used to coordinate care for the member. The data that may be stored in the care coordination database 112 includes the member data 114 obtained by the care coordination device 106, claims data 116 detailing the claims of the members, targeting data 118, coordination data 120 storing the various actions taken by the patient evaluator, and the trigger data 122. The claims data 116 may include prescription claim history of the members of the client. The targeting data 118 may includes a number of queries that may be defined (e.g., by a clinician). The targeting data 118 may be used by the disease management care coordination system to identify members. The coordination data 120 may include data that documents member outcomes. An outcome may be a result of an interaction or response to a therapy prescribed to the member. The coordination data 120 may include interventions, case history, and the like. The trigger data 122 may include data used by the disease management care coordination system 100 to identify problem areas associated with members, such as queries. Trigger data 122 may be a query, rule, policies, or similar method of information retrieval that may include inclusive and exclusive criteria to identify patients. The criteria that may be used to identify patients may include any type of member attribute. For example, a higher dollar spend on medication, members with multiple open cases, and the like may be identified through use of the trigger data 122.

The patient evaluator device 108 may be in communication with a patient evaluator database 124. The patient evaluator database 124 may store patient evaluation data 126 of the members of the client. The patient evaluation data 126 may include labs results, notes by the patient evaluator regarding treatment of the member, member outcomes, or other information that may be derived from the interaction between the patient evaluator and the member.

The care coordination device 106 may be connected with the care coordination integrated database 132 to access and update the integrated data 134 of members, generate various levels of reports, and provide one or more data feeds of the integrated data 134 to users of the system 100. The users of the system may include the client, health management vendor, patient evaluators, and other medical service providers.

Data feeds from devices 102, 106, 108, 142 and databases 110, 112, 124, 128 may be integrated and stored as integrated data 134 in a care coordinator integrated database 132. The integrated database may store data received from various healthcare providers, vendors, and clients to integrate and compile comprehensive data associated with members. The integrated data 134 may include patient profiles compiled from data received from client devices 102, care coordination devices 106, health management vendor devices 142, and/or patient evaluator devices 108. The integrated data 134 may be integrated based upon member identification. In some embodiments, the integrated data 134 may be integrated based upon a combination of information used to identify a member, such as insurance policy number, home address, contact number, or any similar information.

While the system 100 in FIG. 1 is shown to include single devices 102, 106, 108, 142 multiple devices may be used. The devices 102, 106, 108, 142 may be the same type of device or may be different device types. When multiple devices are present, the multiple devices may be of the same device type or may be a different device type. Moreover, system 100 shows a single network 104; however, multiple networks can be used. The multiple networks may communicate in series with each other to link the devices 102, 106, 108, 142 or in parallel to link the devices 102, 106, 108, 142.

Figure 2:
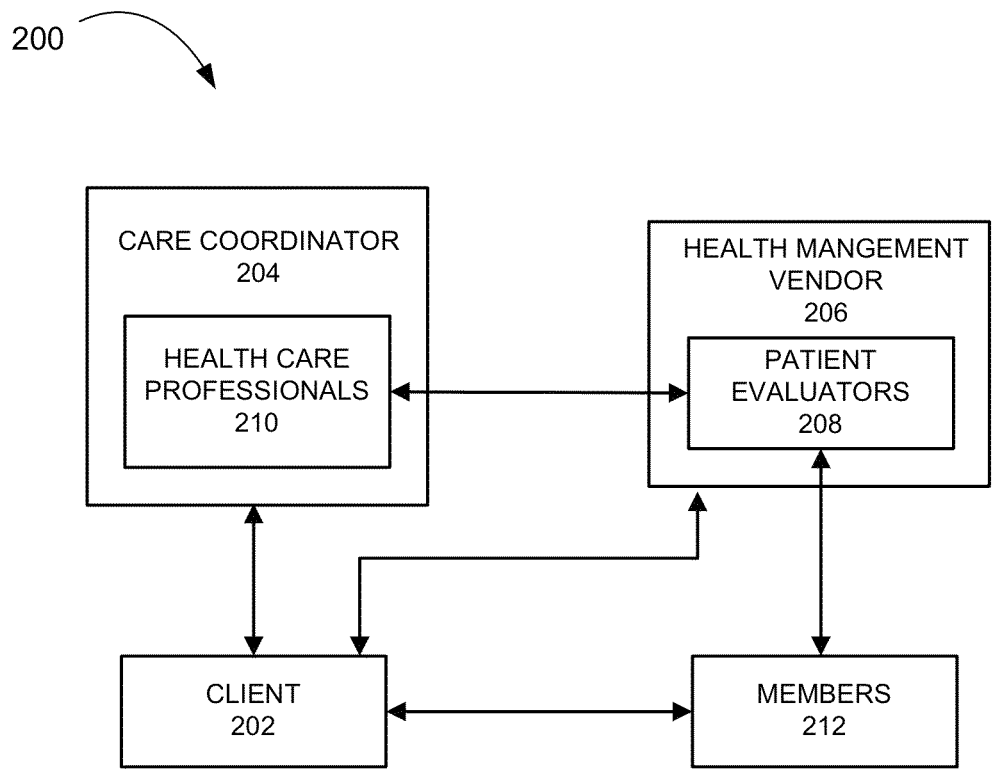
FIGS. 2-4 are block diagrams that illustrate example relationships, according to example embodiments.
Figure 3:
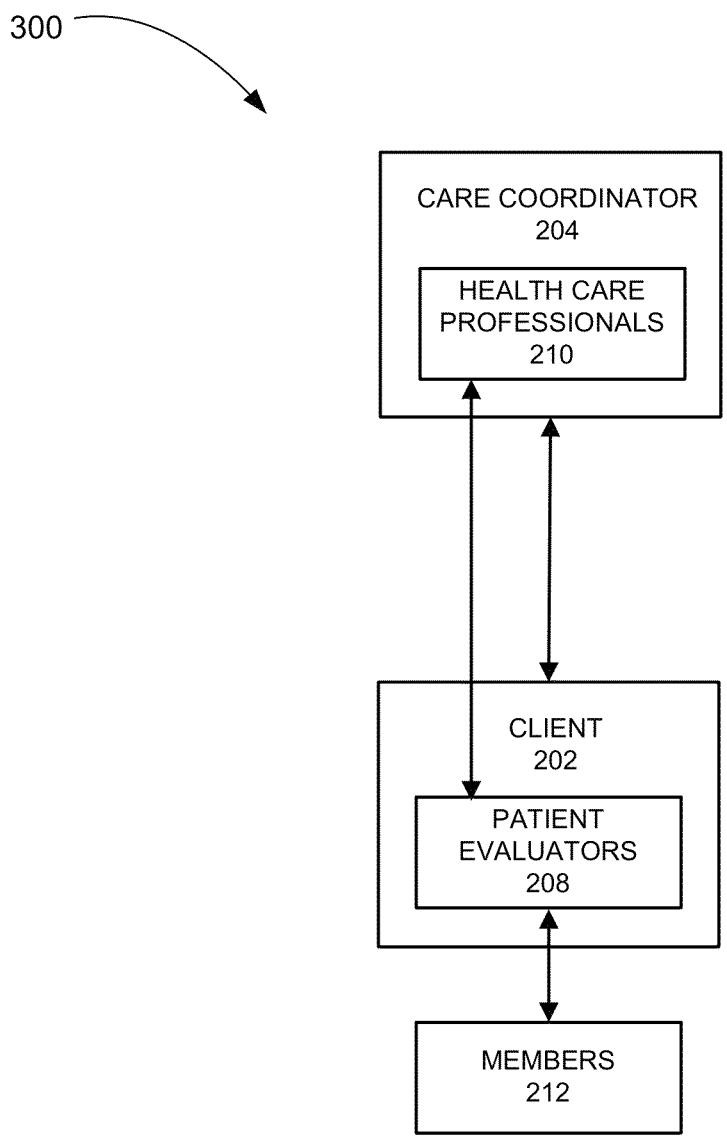
Figure 4:
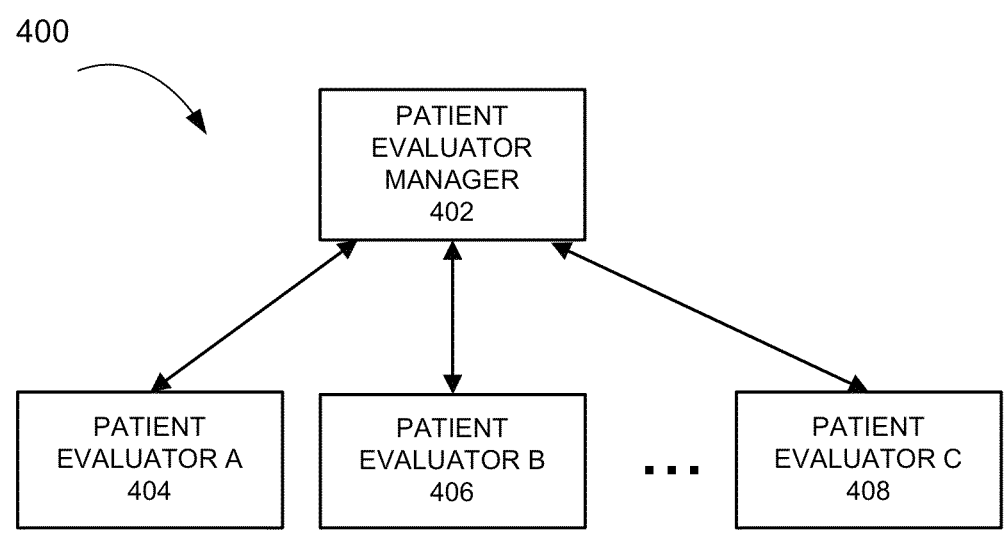

FIGS. 2-4 are block diagrams showing example relationships between various people associated with the system 100. Other types of relationships and different people may be engaged with the system 100 beyond these example relationships.

Relationship 200, depicted in FIG. 2, reflects when a client 202 may be an organization that does not have the clinical abilities to provide healthcare for members 212. Thus, the client may hire one or more health management vendors 206 to provide healthcare for members 212 associated with the client 202. As shown, the client 202 contracts with a care coordinator 204 to provide coordination of care services for members 212 of the client 202 through access to a disease management care coordination system. The members 212 may be employees of the client 202.

The health management vendor 206 that contacts the members 212 of the client 202 may be a disease management vendor. Patient evaluators 208 (e.g., nurses, doctors, or other people) may contact the members 212 to provide health care. The patient evaluators 208 may contact health care professionals 210 (e.g., pharmacists) to obtain additional information that may be used to provide heath care services for members 212.

Members 212 may be employees of the client 202 or otherwise associated with the client 202 and have received some type of medical and/or pharmaceutical benefit through a health plan associated with the client 202.

Relationship 300, depicted in FIG. 3, depicts when the client 202 may have its own patient evaluators 208 and thus does not use a health management vendor 206. For example, a health care organization that has a health plan may engage the care coordinator 204 to obtain access to the care coordination subsystem 502.

Relationship 400, depicted in FIG. 4, depicts when there are multiple patient evaluators associated with the health management vendor 206 (e.g., disease management vendor) (or directly with the client 202). In some embodiments, a patient evaluator manager 402 manages the case load of various patient evaluators 404-408. Patient evaluator manager 402 may receive identified cases of members 212 and assign the cases to patient evaluators 404, 406, 408.

Figure 5:
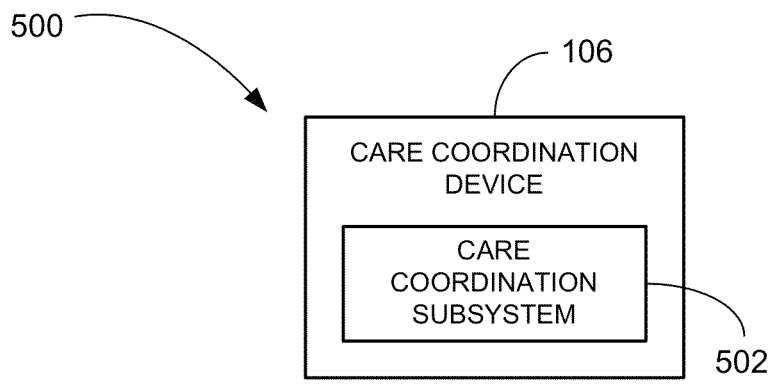
FIG. 5 illustrates an example care coordination device that may be deployed in the system of FIG. 1, according to an example embodiment.

FIG. 5 illustrates the care coordination device 106, according to an example embodiment. The care coordination device 106 may include a care coordination subsystem 502. The care coordination subsystem 502 may be a computerized tool that enables the patient evaluators 208 to efficiently manage cases of the members 212. Through use of the care coordination subsystem 502, the patient evaluators 208 may have more information about the member available faster. Thus, the patient evaluators 208 may be able to provide better care to members 212 through use of the care coordination subsystem 502.

The care coordination subsystem 502 may have all the functionality on the care coordination device 106, some of the functionality on the care coordination device 106 and other devices (e.g., 102, 108, 142), or all the functionality on other devices 102, 108, 142. The care coordination subsystem may be implemented as a think client, a thick client, peer-to-peer or otherwise. In some embodiments, access to the care coordination subsystem may be based on the role of the person accessing the care coordination subsystem 502.

The care coordination device 106 with the care coordination subsystem 502 may be deployed in the system 100, or may be deployed in another system.

Figure 6:
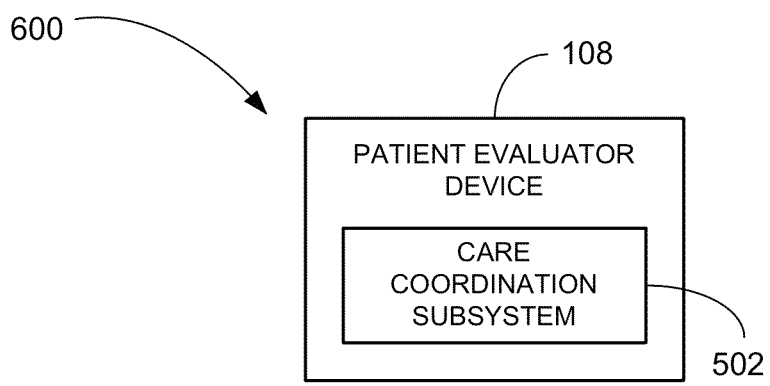
FIG. 6 illustrates an example patient evaluator device that may be deployed in the system of FIG. 1, according to an example embodiment.

FIG. 6 illustrates the patient evaluator device 108, according to an example embodiment. The patient evaluator device 108 includes a care coordination subsystem 502. The patient evaluator device 108 with the care coordination subsystem 502 may be deployed in the system 100, or may be deployed in another system.

Figure 7:
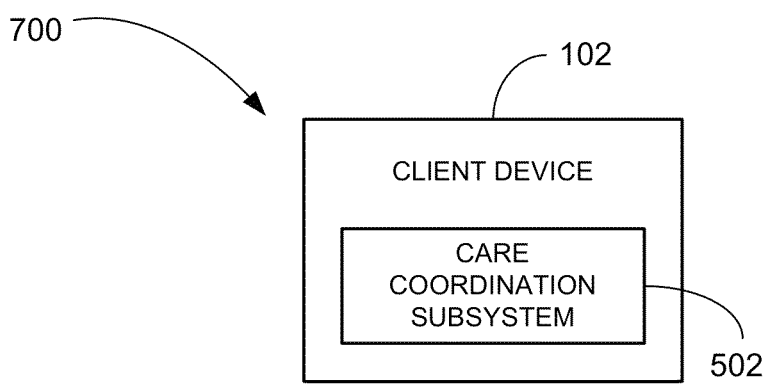
FIG. 7 illustrates an example client device that may be deployed in the system of FIG. 1, according to an example embodiment.

FIG. 7 illustrates the client device 102, according to an example embodiment. The client device 102 includes a care coordination subsystem 502. The client device 102 with the care coordination subsystem 502 may be deployed in the system 100, or may be deployed in another system.

In some embodiments, the system 100 may include a health management vendor device 108 which may include a care coordination subsystem 502. The health management vendor device 108 with the care coordination subsystem 502 may be deployed in the system 100, or may be deployed in another system.

Figure 8:
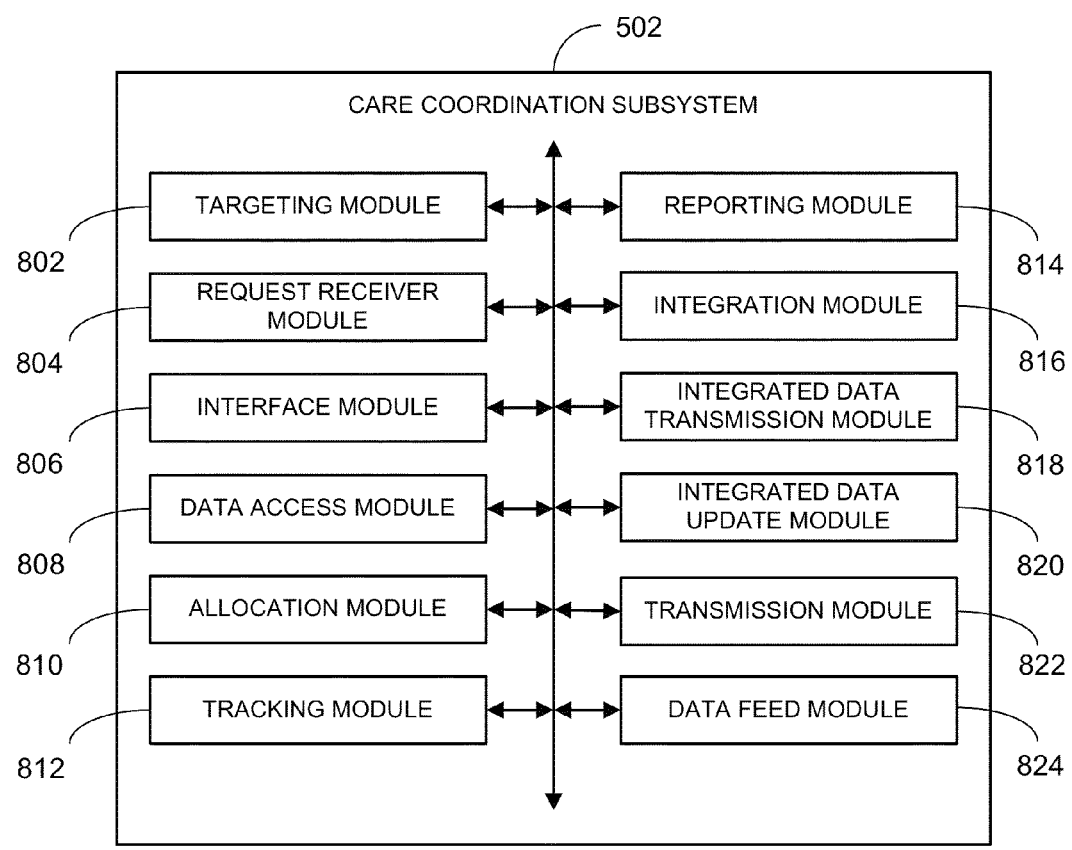
FIG. 8 is a block diagram of an example care coordination subsystem that may be deployed with the care coordination device of FIG. 5, the patient evaluator device of FIG. 6, and/or the client device of FIG. 7, according to example embodiments.

FIG. 8 illustrates an example disease management care coordination subsystem 502 that may be deployed in the client device 102, care coordination device 106, patient evaluator device 108, health management vendor device 142, or otherwise deployed in another system. One or more modules are communicatively coupled and included in the disease management care coordination subsystem 502 to enable disease management care coordination. The modules of the disease management care coordination subsystem 502 that may be included are a targeting module 802, a request receiver module 804, an interface module 806, a data access module 808, an allocation module 810, a tracking module 812, a reporting module 814, an integration module 816, an integrated data transmission module 818, an integrated data update module 820, a transmission module 822, and/or a data feed module 824. Other modules may also be included. In some embodiments, the care coordination subsystem 502 may be a web-based tool.

In some embodiments, the modules of the disease management care coordination subsystem 502 may be distributed so that some of the modules are deployed in care coordination device 106 and some modules in the patient evaluator device 108 and/or health management vendor device 142. In one embodiment, the modules are deployed in memory and executed by a processor coupled to the memory. The functionality contained within the modules 802-824 may be combined into a lesser number of modules, further divided among a greater number of modules, or redistributed among existing modules. Other configurations including the functionality of the modules 802-824 may be used.

In some embodiments, the care coordination subsystem 502 may be a closed tool, requiring users of the system to access the subsystem 502 using a care coordination subsystem client (not shown). One or more modules may be communicatively coupled and included in the care coordination subsystem 502 to enable coordination of care of a member.

In some embodiments, the modules of the care coordination subsystem 502 may be distributed so that the modules are deployed in one or more of the client device 102, the care coordination device 106, the patient evaluator device 108, and health management vendor device 142. In one embodiment, the modules are deployed in memory and executed by a processor coupled to the memory.

The care coordination subsystem 502 may be used by the patient evaluators 208 to prioritize cases for providing health care services. The prioritization may enable the patient evaluators 208 to focus on giving better care.

The health care services provided by the patient evaluators 208 may drive behavior changes to improve health of the members 212.

In some embodiments, the care coordination subsystem 502 is implemented as a care coordination tool by which the patient evaluators 208 may access through their patient evaluator devices 108. At least a portion of the functionality of the care coordination subsystem 502 may be implemented within the care coordination device 106.

The targeting module 802 may run targeting on the claims data 116 using the targeting data 120. The targeting may be run weekly or with a different frequency to identify cases. The targeting may include a number of queries that may be defined (e.g., by a clinician). Targeting may then be used to identify members 212 according to different attributes. Attributes may include, but are not limited to, disease states, geographic location, medication received, type of health insurance, or other type of information associated with members.

The targeting may not be immediately run to enable time for changes to the claims data 116 due to error or other problems. In some embodiments, by running the targeting on the claims data 116 that is recent, the patient evaluator 208 can have access to timely information about the members 212. In some embodiments, providing more timely information to the patient evaluator 208 provides a greater chance that the member 212 will be receptive to or otherwise adopt the information and/or advice provided by the patient evaluator 208.

Examples of results of targeting include identifying members 212 who may need help with a first time medication, members 212 who fill a prescription late, an abnormal behavior pattern for filing a prescription by members 212, or the like.

The request receiver module 804 may receive an evaluation request. The evaluation request may be to evaluate a case that has been identified through the targeting. In some embodiments, the evaluation request may be to evaluate multiple cases identified through the targeting. The evaluation request may be made prior to the patient evaluator 208 contacting the member 212. The request receiver module 804 may also generate a response to the received evaluation request. In some embodiments, a filter-setting request may be received by the request receiver module 804. Generation of the display is then based on running the targeting, receipt of the query request, and receipt of the filter-setting request. The filter setting request may include a target, a disease state, or both the target and the disease state.

The interface module 806 may generate a display in response to receiving a generation request based on running the targeting and receipt of the query request. The generated display may present information used by the patient evaluators 208 to provide case management on behalf of the members 212.

By way of example, if a member 212 has been newly prescribed cholesterol medication, and the member 212 may receive a call from a patient evaluator 208 during the first week of use of the medication to determine whether the member 212 is having any side effects based on the information received through the generated display by the interface module 806, the member 212 is more likely to communicate with the patient evaluator 208 then if the patient evaluator 208 contacts the member 212 six weeks after starting the new medication.

In some embodiments, the timely manner may in which the patient evaluator 208 contact the members 212 may increase the number of members 212 enrolling in appropriate disease management programs.

The data access module 808 may access the trigger data 122. Generation of the display is then based on running the targeting, receipt of the query request, and accessing the trigger data 122.

The allocation module 810 may be deployed within the care coordination subsystem 502 to receive a case designation and associate a case of a member 212 to a patient evaluator 208. In some embodiments, the allocation module 810 may associate the member 212 with a case designation responsive to the targeting. In some embodiments, the allocation module 810 may associate the member 212 with multiple case designations responsive to the targeting.

The tracking module 812 may be deployed within the care coordination subsystem 502 to receiving a case indication of a case and storing the coordination data 122 associated with the case in the care coordinator database 112 based on receipt of the case indication. In some embodiments, the tracking module 812 may receive and store the association of case designations and patient evaluators 208.

Reporting module 814 may generate and transmit a report over the network 104. The report may be transmitted to the client device 102 or a different device. When deployed, the reporting module 814 generates reports for the care coordination subsystem 502. In some embodiments, the generated reports may include a report based on the coordination data 122 of a single member or multiple members. The generated report on the single member may be at an operational level report. The generated report on multiple members may be at a summary level report. The summary level report may include, by way of example, a number of cases that have been closed during a period of time. In some embodiments, the client 202 may use the reports to look over months to see the trends and track the progress of the patient evaluators. In some embodiments, the reports generated by the reporting module 814 include an outcomes report. The outcomes reports includes activity done based on the program may identify downstream impact of the coordination of care. The outcomes report may reveal whether the rates of hospitalizations were reduced for the members.

An integration module 816 deployed within the care coordination subsystem 502 integrates data from multiple data feeds received from a client device 102, a care coordination device 106, patient evaluator device 108, and/or health management vendor device 162.

The data feed from the client device 102 may include member data 114 may include demographic data, contact information, health insurance data, and other types of personal data associated with members. Member data 114 may be retrieved from the client database 110.

The data feed from the care coordination device 106 may include the member data 114 obtained by the care coordinator, claims data 116 detailing the claims of the members, targeting data 118, coordination data 120 storing the various actions taken by the patient evaluator, and the trigger data 122. The claims data 116 may include prescription claim history of the members of the client. The targeting data 118 may includes a number of queries that may be defined (e.g., by a clinician). The targeting data 118 may be used by the disease management care coordination system to identify members. The coordination data 120 may include data that documents outcome. The coordination data 120 may include interventions, case history, and the like. The trigger data 122 may include data used by the disease management care coordination system 100 to identify problem areas associated with members, such as queries.

The data feed from the patient evaluation device 108 may include patient evaluation data 128 or health data which may include labs results, notes by the patient evaluator regarding treatment of the member, member outcomes, or other information that may be derived from the interaction between the patient evaluator and the member.

An integrated data transmission module 818 may be deployed within the care coordination subsystem 502 to transmit the integrated data associated with a member 212 to a patient evaluator device 108.

An integrated data update module 820 may be deployed within the care coordination subsystem 502 to update the integrated data 134 using additional member information received from the patient evaluator 208. The additional information may include lab results, clinical notes, outcomes from member interactions, or other data that may be derived from the interaction between the patient evaluator and the member. In some embodiments, the integrated data update module may update the integrated data 134 using information received from other medical services providers, such as pharmacists or specialists (e.g., disease specialist).

A transmission module 822 may be deployed within the care coordination subsystem 502 to transmit a patient profile to a medical services provider. The patient profile may include trigger data 122 and the integrated data associated with the member.

A data feed module 824 may be deployed within the care coordination subsystem 502 to transmit or otherwise provide a data feed of the integrated data 134.

Data feeds from devices 102, 106, 108, 142 and databases 110, 112, 124, 128 may be integrated and stored as integrated data 134 in a care coordinator integrated database 132. The integrated database may store data received from various healthcare providers, vendors, and clients to integrate and compile comprehensive data associated with members. The integrated data 134 may include patient profiles compiled from data received from clients, care coordinators, and health management vendors. The integrated data 134 may be integrated based upon member identification. In some embodiments, the integrated data 134 may be integrated based upon a combination of information used to identify a member, such as insurance policy number, home address, contact number, or any similar information.

Figure 9:
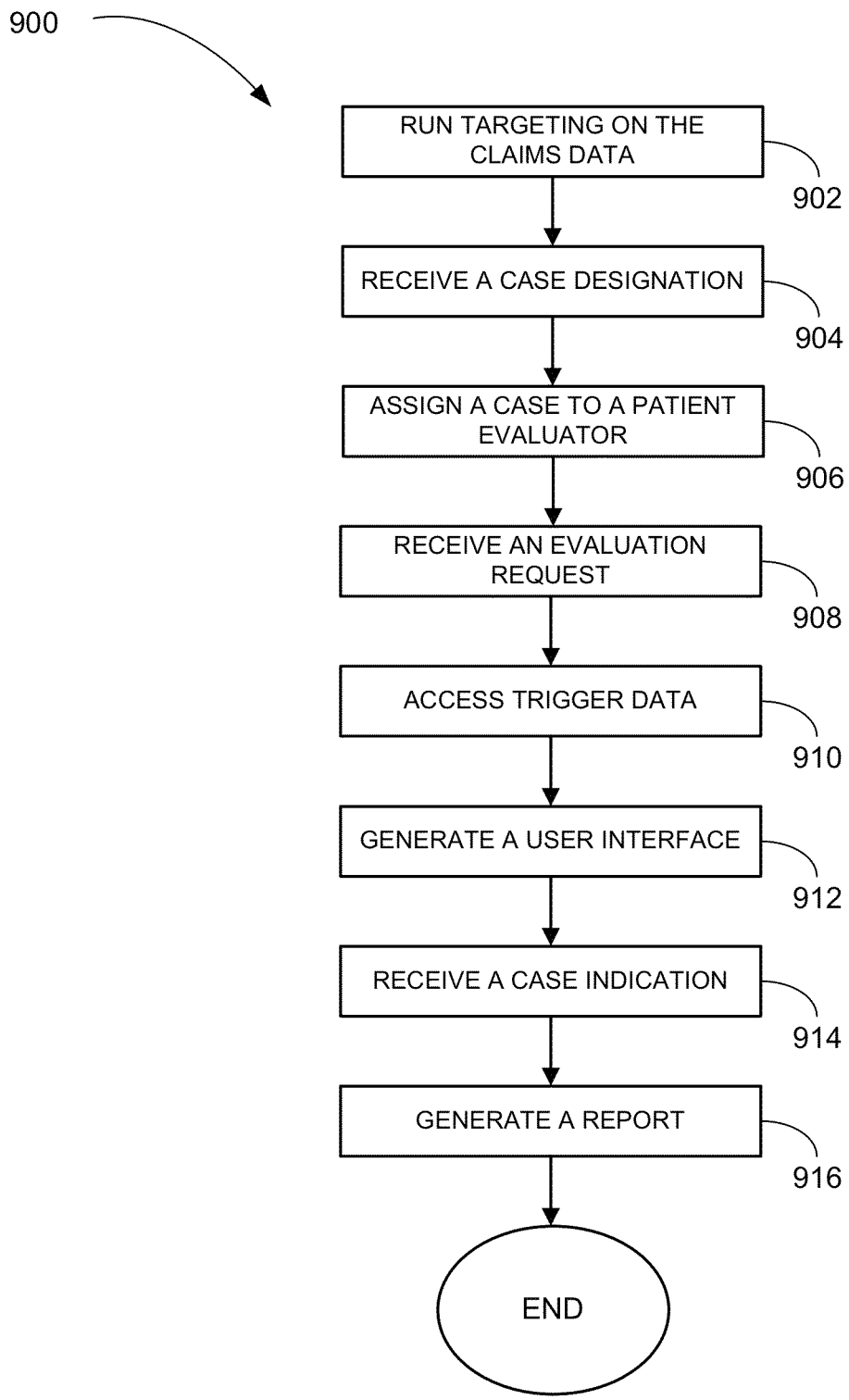
FIG. 9 is an example process flow illustrating a method for care coordination, according to an example embodiment.

FIG. 9 illustrates a method 900 for disease management care coordination according to an example embodiment. The method 900 may be performed by the care coordination device 106, partially by the care coordination device 106 and partially by the client device 102 and/or the patient evaluator device 108, or may be otherwise performed.

Targeting is run on the claims data 116 at block 902 using the targeting data 120. In some embodiments, targeting may include mining data associated with members 212 to identify different member opportunities. Data associated with members may include claims data 116 (e.g., pharmacy claims data and/or medical claims data), clinical data, member data 114, lab results data, and/or data received from a wellness vendor. Targeting may be run or executed by the care coordination device 106. Targeting may be run or executed on a periodic basis. In some embodiments, the periodic basis for running or executing the target data may include allowing for reversals. Reversals occur when a claim may be reversed. Claims may be reversed for various reasons, such as the member not receiving a prescription drug, the member returning the prescription drug due to side effects or expense, or a pharmacy mistake.

For example, a care coordination device 106 may initiate a first fill targeting. The first fill targeting may identify members 212 who have never used a particular drug. The criterion used to identify the members 212 in the first fill targeting may include determining if the member 212 has used the drug within 360 days of therapy. Other criteria that may be used for the first fill targeting may include recent reversals made by the member and whether the member was previously identified in a recent first fill targeting.

A case designation may be received at block 904. The case designation may be received from the patient evaluator manager 402 through the patient evaluator device 108. The case designation may be provided to the care coordination device 106 and may be stored in the care coordinator database 112 as coordination data 122.

A case designation may be an identifier of a case. In some embodiments, each unique case identified by the targeting may be assigned a case designation. In some embodiments, the case designation may be assigned by the care coordination subsystem 502. The case designation may provide a mechanism to track the case in the disease management care coordination subsystem 502, so that any entity or affiliate of the disease management care coordination subsystem 502 may access and track the case easily. In some embodiments, a single member 212 may have multiple case designations. The multiple case designations may represent the multiple member opportunities as identified by the care coordination system. The multiple case designations may be assigned responsive the different disease states of the member 212 or different targets run by the care coordinator. For example, the care coordinator 204 may run a first targeting to identify members 212 with high blood pressure and member A may be listed in the results of the targeting. Member A may be assigned case designation 123. If the care coordinator then runs a second targeting to identify members with type II diabetes and member A may be listed in the results of the targeting, then Member A may receive a second case designation 234. Then case designation 123 identifies Member A as having high blood pressure and case designation 234 identifies Member A as having type II diabetes.

The cases and case designations may be transmitted to the health management vendor device 142. The health management vendor device 142 may be used to evaluate the cases. In some embodiments, the health management vendor 206 may evaluate the cases by using filters or applying various criteria to the cases to organize or prioritize the received case designations.

A case of a member associated with the client 202 may be assigned to a patient evaluator (e.g., the patient evaluator 404) at block 906. In some embodiments, the patient evaluator manager 402 selects the patient evaluator to be associated with the case. The device (e.g., the care coordination device 106) then makes the association and stores the association in the coordination database 112 as coordination data 122. In some embodiments, the association may be transmitted to the care coordinator integrated database 132 as integrated data 134. In some embodiments, the patient evaluator device 108 automatically selects the patient evaluator 208 to be associated with the case. The automatic selection may be based on experience of the patient evaluators 208, background of the patient evaluators 208, caseload of the patient evaluators 208, or the like. A single factor or multiple factors may be used in making the automatic selection.

Using the disease management care coordination subsystem 502, the health management vendor 206 may assign the cases to patient evaluators 208 through a health management vendor device 142. Health management vendors may assign cases by member 212 (e.g., all case designations associated with member A may be assigned to Patient Evaluator X) or they may assign cases by opportunity type or other criteria (e.g., all case designations for diabetic members may be assigned to a diabetic expert). The disease management care coordination subsystem 502 may transmit the assignment of the cases to patient evaluators 208 to the care coordinator integrate database 132, where parties may access the information with access to the disease management care coordination subsystem 502 and sufficient privileges. In some embodiments, a user of the disease management care coordination subsystem 502, assuming they have sufficient rights and privileges, may generate a report listing all case designations assigned to a patient evaluator 208, listing all case designations for a member 212, or listing all case designations associated with a disease state, member opportunity, or other criterion.

Once a case has been assigned to a patient evaluator, the patient evaluator 208 may have several options. A patient evaluator 208 may log into the disease management care coordination subsystem 502 to view all the cases that have been assigned to them. The patient evaluator may review each case and take appropriate actions. For instance, the patient evaluator 208 may review a case and determine that the next step may be to contact the member 212. Once the member 212 has been contacted, the patient evaluator 208 may make a notation in the disease management care coordination subsystem 502. The notation made by the patient evaluator 208 may be transmitted over the network 104 to the care coordinator integrated database 132 so that the next person who accesses the information associated with the member 212 will have access to the notations made by the patient evaluator 208.

If the patient evaluator 208 determines that there may be an issue that needs specialized care, the patient evaluator may generate an evaluation request using the disease management care coordination subsystem 502. For example, if, while the patient evaluator 208 is reviewing a case, the patient evaluator 208 determines that they need further information from a pharmacist, the patient evaluator 208 may generate an evaluation request by selecting a button in the disease management care coordination subsystem 502. The patient evaluator may then send a message through the disease management care coordination subsystem 502 to an available pharmacist regarding the case. In some embodiments, the evaluation request may include the information associated with the case. In some embodiments, the evaluation request may include a note or question from the patient evaluator 208 and the case designation.

The evaluation request may be received at block 908. The specialist, healthcare provider, and/or a medical services provider receiving the evaluation request may review the request. The evaluation request may include the case designation. The pharmacist may enter the case designation into the disease management care coordination subsystem 502 that would then display a comprehensive member profile that may include claims history, medical history, lab results, or other type of available information in the disease management care coordination subsystem 502. The healthcare provider or specialist may use the case designation to display within the disease management care coordination subsystem 502 to access trigger data 122 at block 910.

Trigger data 122 may include any other open case designations associated with the member as well as historical case designations that may be accessed by the disease management care coordination subsystem 502. Evaluation requests may be generated responsive to questions arising from multiple open triggers of a member 212 that may increase the complexity of the medical issues of the member 212.

A case designation for a member 212 may indicate that the case designation may be a polypharmacy case. The trigger data 122 may be that the member 212 is taking eight maintenance drugs concurrently. If a patient evaluator 208 assigned to the case reviews the case and determines that they need the assistance of a pharmacist, the patient evaluator generates an evaluation request with a specific question or request and the case designation. The pharmacist may receive the evaluation request and the case designation and enters the case designation in the disease management care coordination subsystem 502. The disease management care coordination subsystem 502 may display a case designation for a first fill trigger, a case designation for medication adherence, and a case designation for polypharmacy within the past two months. Thus, the pharmacist would be accessing multiple triggers for a member 212 to evaluate the multiple pharmacy opportunities of the member within the care coordination subsystem 502.

A display may be generated at block 912. The display may be generated based on running the targeting, receipt of the query request, and/or accessing the trigger data 122. In some embodiments, responsive to accessing 910 trigger data 122, a display may be generated to display the patient profile of the current case. In some embodiments, the historical case designations are also displayed in the generated display. The historical case designations may be displayed in a separate tab. In some embodiments, other data associated with the member 212 may also be displayed in the display, such as the claims data 116 or other health data for the member 212. The generated display may include the latest information associated with the member 212, such as the latest claims data 116 or other health data for the member 212, and displaying the data in a manner that permits the user to utilize the information without being overwhelmed by the volume of information. By generating different visual aids in the display, such as graphs and charts, the user may be presented with a great deal of comprehensive information about the medical condition of the member 212, related open triggers, and historic medical data.

By providing the pharmacist or any other user of the disease management care coordination subsystem 502 with a comprehensive patient profile, the pharmacist and other users may better address the current problems by understanding the context of the current problem. The disease management care coordination subsystem 502 may be used to create linkages between different triggers and case designations. The disease management care coordination subsystem 502 may be used to document the steps taken by the pharmacist, patient evaluator, or other use of the disease management care coordination subsystem 502 after evaluating the patient profile of the member. For example, the pharmacist, responsive to the evaluation request and reviewing the patient profile of the member, may communicate with the patient evaluator or directly with the member. Any action taken by the pharmacist, patient evaluator, or other user may be documented using the disease management care coordination subsystem 502. The documentation of the actions of the users may be transmitted to the care coordinator integrated database 132 so that the next user may be able to access the updated comprehensive patient profile of the member 212 to ensure quality treatment for the member 212.

In some embodiments, a filter-setting request may be received. The generation of the display may then further receipt of the filter setting request.

A case indication of a case may be received from the patient evaluator at block 914. The case indication may be received from the patient evaluator associated with the case. The case indication may indicate that the next course of action for the member, notes on the case from the patient evaluator, or the like. The case indication may be received from the patient evaluator through the patient evaluator device 108. The case indication may be provided to the care coordination device 106 and may be stored in the care coordinator database 112 as coordination data 122.

A report may be generated at block 916. In some embodiments, the report may be an outcomes report. In some embodiments, the report may be generated based on the coordination data 122. The report may then be transmitted over the network 104 to the client device 102. The generated report may include an operational level report, a summary level report, or both the operational level report and the summary level report.

In some embodiments, the integrated data may be readily accessible to any user utilizing the care coordination subsystem 502 and can use the information to create linkages in the patient profile of the member and propose better or different treatment based upon the comprehensive patient profile. In some embodiments, the integrated and updated data may be used to generate various levels of reports. In some embodiments, the integrated and updated data may be available as a data feed to one users of the care coordination subsystem 502.

One example of the type of reporting available from the subsystem 502 may be that if a process change is made, either internally or by a health management vendor, the care coordination subsystem 502 may measure the result and impact of the change by generating a macro-level report of the member population of a client 202.

In some embodiments, the information displayed in the display may be copied. The information may then be pasted into a tool associated with the client 202.

In some embodiments, criteria may be provided by the patient evaluator 208 to the disease management care coordination subsystem 502. The criteria may be used to narrow down the results of a query run to provide applicable cases. The criteria may be displayed in the display. A single criterion or multiple criteria may be used.

FIGS. 10-16 depict example displays according to example embodiments of the care coordination subsystem 502. The ovals indicated on FIGS. 12-15 indicate the tab of the interface that the screen is displaying. The displays 1000-1600 include example data and may be generated by the disease management care coordination subsystem 502 and ultimately presented to a variety of the users of the system 100. The displays may be presented via the disease management care coordination subsystem 502. However, other types of displays and modification to the displays 1000-1600 may also or alternatively be presented. The displays 1000-1500 may be presented to patient evaluators 208 and the displays 1000-

1600 may be presented to the patient evaluator manager 402. Users of the disease management care coordination subsystem 502 may be any person associated with the client 202, care coordinator 204, or health management vendor 206. Users may include patient evaluators 208 and health care professionals 210.

Figure 10:
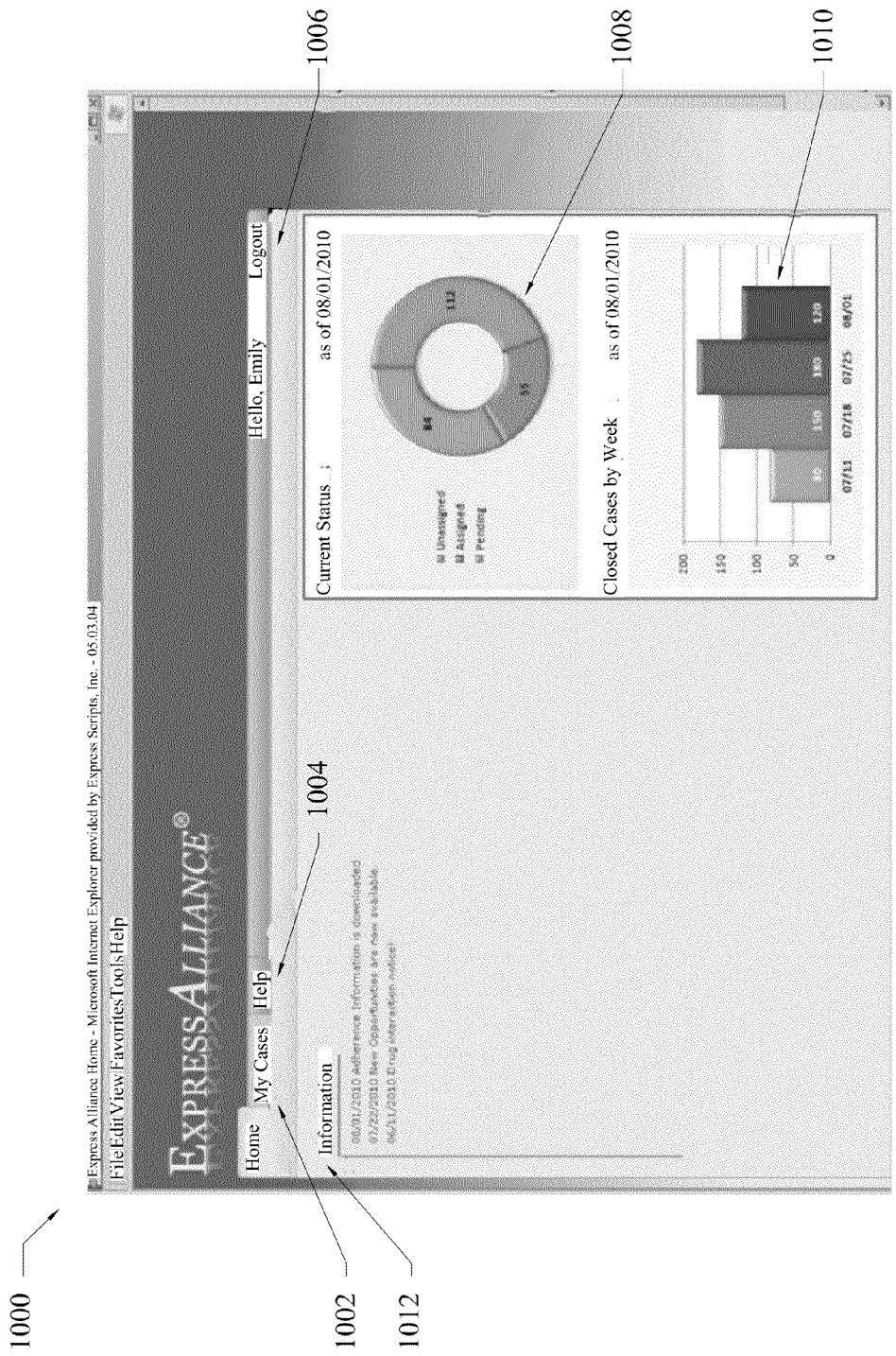

Display 1000, illustrated in FIG. 10, depicts a home screen to a user. The user may select additional tabs to see different content from the home screen. These tabs include MY CASES tab 1002 and HELP tab 1004. The user can also select LOGOUT link 1006 to log out.

Display 1000 may graphically display the status of a number of cases associated with the user as of a particular date (e.g., doughnut graph 1008). In this example, eighty-four cases are pending, fifty-five cases are assigned, and one hundred and twelve cases are unassigned as of Aug. 1, 2010. The status may be updated daily (e.g., at midnight), or may be updated with a different frequency.

Display 1000 may graphically display an information section that may display critical notices or upcoming deadlines for the group (e.g., Information Section 1012).

Display 1000 may graphically display the number of cases closed by week as of a particular date (e.g., bar graph 1010). In this example, eighty cases were closed during the week of July 11, one hundred and fifty cases were closed during the week of July 18, one hundred and eighty cases were closed during the week of July 25, and one hundred and twenty cases were closed during the week of August 1. While the prior four weeks are shown in the display 1000, more or less weeks may be shown.

Once the user selects MY CASES tab 1002 in display 1000, display 1100 (depicted in FIG. 11) may be presented to the user. Display 1100 may include a number of sub links that may be selected to view content (depicted in FIGS. 12-15). Displays 1100-1500 respectively show the content presented when the VIEW CASES sub link 1102, PATIENT INFO sub link 1202, INVERVENTION sub link 1302, CLAIM HISTORY sub link 1402, and ACTIONS sub link 1502 are selected. Other displays besides the display 1000 may be the default screen when MY CASES tab 1002 is selected.

Figure 11:
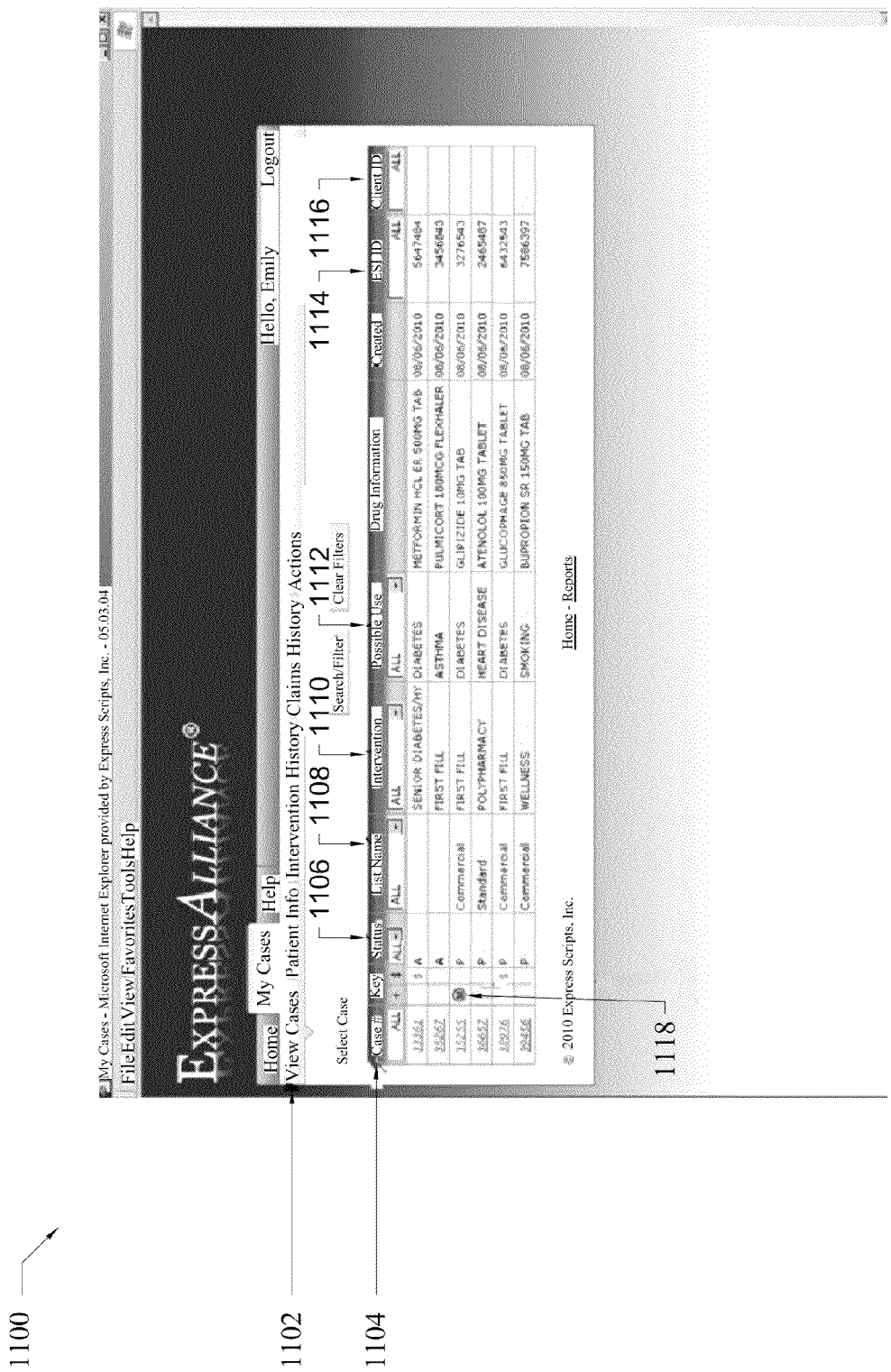
Figure 12:
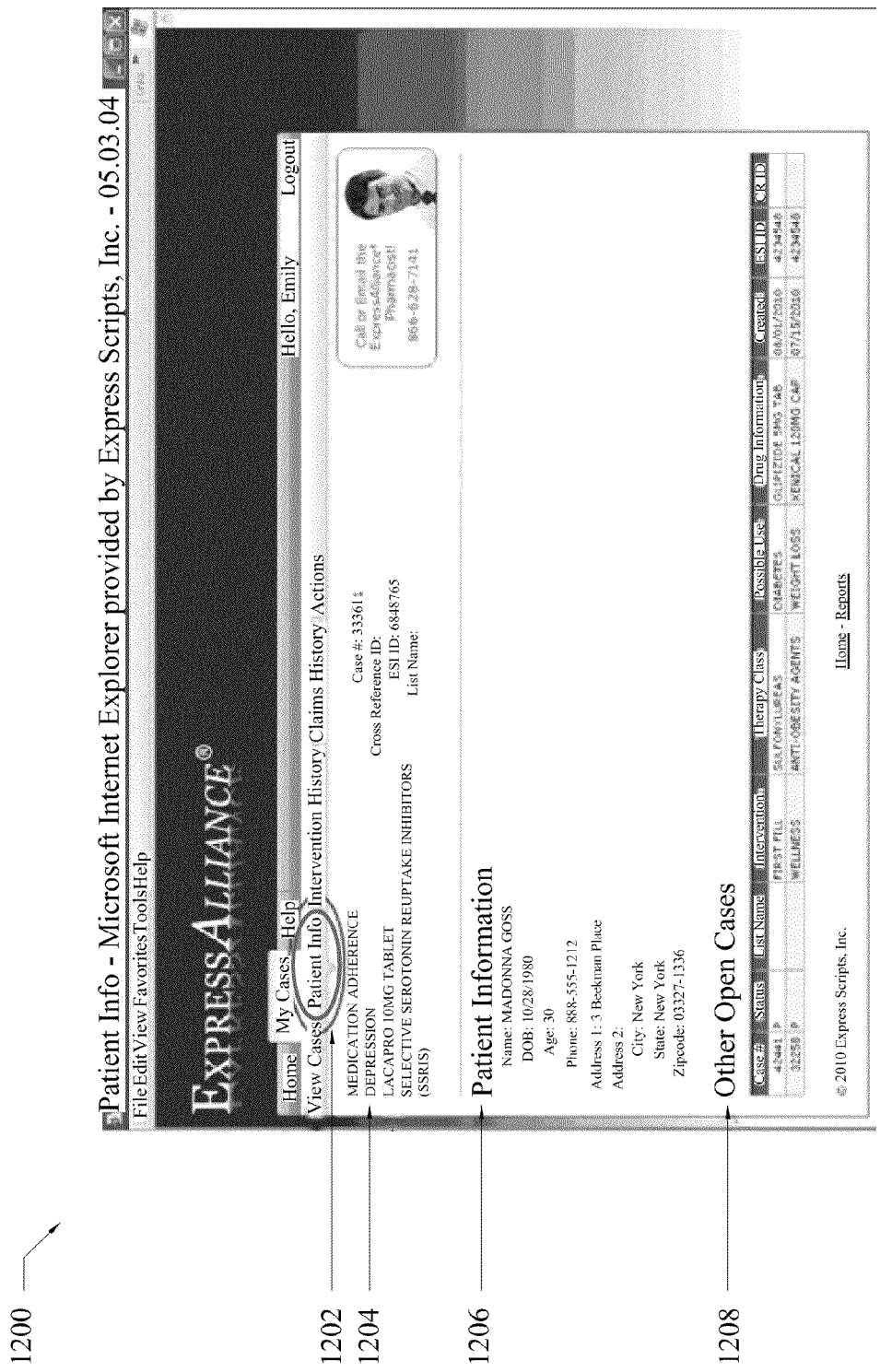
Figure 15:
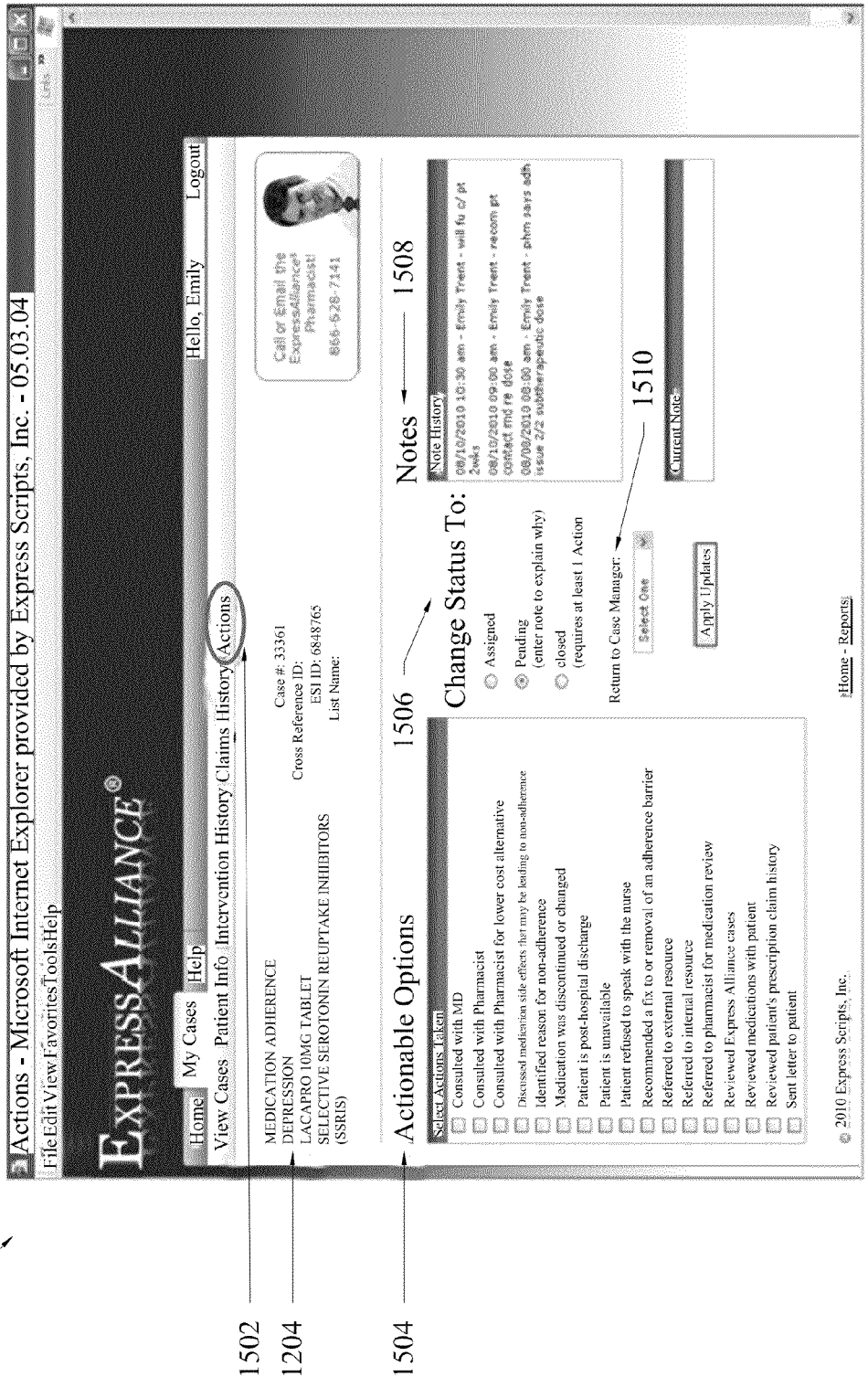

The display 1100, shown in FIG. 11, presents the cases associated with the user to the patient evaluator. The user may perform searches and filtering by selection of various buttons. The user may also search by case designation 1104. Through various drop down menus, the users may filter by status 1106, list name 1108, intervention 1110, possible use 1112, care coordinator ID 1114, and client ID 1116. The user may filter using other attributes, such as drug information, date created, and other attributes that may be associated with the case designation and displayed in the subsystem 502.

Examples of status 1106 may include "A" for assigned, "C" for closed, and "P" for pending. The list name may be defined by the client 202 or otherwise defined. For example, the available list names may include advanced, commercial, standard, and express. The drug information and the creation date may also be presented. In some embodiments, the cases that have been in the system beyond a certain number of days (e.g., thirty days, forty five days, sixty days, seventy five days, or ninety days) may expire and then no longer be presented in the next viewing of the display.

In addition, the display 1100 may identify certain members through use of a dollar sign logo (not shown) as being a member that has exceeded a certain dollar threshold for drug cost. The drug cost may be actual dollars spent on various drugs, the ingredient cost of the drug, or otherwise. The amount of the threshold may be adjusted or set by the client 202, the health management vendor 206, or may be otherwise be adjusted or set. In addition, the amount of spend by a member 212 may be tracked on an annual basis, or through a different period of time (e.g., semiannually). In some embodiments, a number of dollar signs may be used to indicate a relative level of severity.

Display 1100 may identify certain members as having multiple cases through use of an "M" logo 1118. The use of the dollar sign logo and/or the "M" logo 1118 may be used to identify members with whom contact may be sought. These members may be considered high risk by the user.

Display 1200 may be presented when PATIENT INFO sub link 1202 is selected. Display 1200 may include information about the member 212 including case information 1204, patient information 1206, other open cases 1208 associated with the member 212. Display 1200 may enable the user to view a more comprehensive profile of the member 212 prior to potential contact. Case information 1204 may include a case designation, intervention type, therapy class, possible use, drug information, diagnosis of the member, medication prescribed to the member, care coordinator ID, and other information that may be associated with the case. Patient information 1206 may include the name of the member, date of birth of the member, age of the member, contact information of the member, address of the member, and other information associated with the member. Other open cases 1208 associated with the member may include a table or other method of organization that includes data related to a case, listed in an organized matter. In some embodiments, each case listed in the open cases 1208 portion of display 1200 may also include a hyperlink to the case, so that when the hyperlink is clicked by the user, information associated with the selected case will be displayed by the care coordination subsystem 502.

Display 1300 may be presented when the INTERVENTION HISTORY sub link 1302 is selected. Display 1300 may present information about intervention actions or contact made by the user or other users with the member. The information displayed to the member in display 1300 includes case information 1204, as described above. Display 1300 may display an Intervention History 1308 that may include Case Designations of cases associated with the client for intervention, List Name, Intervention, Therapy Class, Possible Use, Drug Name, Case Worker (e.g. patient evaluator), Care Coordinator ID, and Client ID. Sections for case outcomes 1304 and case note history 1306 may also be included in display 1300. The case outcomes 1304 section may display information related to actions and outcomes taken concerning the member. In some embodiments, the case outcomes 1304 may display information from the intervention history and cases listed in the intervention history. The case note history 1306 section of display 1300 may include notes entered by a patient evaluator assigned the case, including dates and times actions were taken related to the case.

Display 1400 may be presented when CLAIMS HISTORY sub link 1402 is selected. The information displayed to the member in display 1400 may include case information 1204, as described above. The claims history section 1404 of display 1400 may include a table or other organization structure containing historic claims data for the member displayed to the user. The example information presented to the user in the display 1400 includes fill date, pharmacy, NABP, drug information, quantity, day supply, physician, therapy class, and possible use.

After reviewed of appropriate displays, the user may be ready to take an action and document the action taken through display 1500. Display 1500 may thus be presented when ACTIONS sub link 1502 is selected. The information displayed to the member in display 1500 may include case information 1204, as described above.

Display 1500 may include an ACTIONABLE OPTIONS section 1504. The care coordinator subsystem 502 may generate a list of actions taken and display them in the ACTIONABLE OPTIONS section 1504 of display 1500. The user may select one or more actions displayed in the ACTIONABLE OPTIONS section 1504 of display 1500. The example actions presented to the user in display 1500 may include, but are not limited to: consulted with MD, consulted with pharmacist, consulted with pharmacist for lower cost alternative, discussed medication side effects that may be leading to non-adherence (e.g., failing to refill a prescription drug), identified reason for non-adherence, medication was discontinued or changed, member is post-hospital discharged, member is unavailable, member refused to speak with nurse, recommended a fix or removal of an adherence barrier, referred to external resource, referred to internal resource, referred to pharmacist for medication review, reviewed cases (e.g., as reviewed by Express Scripts, Inc. in accordance with its services offered under the ExpressAlliance™ brand), reviewed medications with the member, reviewed prescription claim history of the member, and sent letter to the member. The user may select (e.g., by selecting a click box) one action or multiple actions from the display.

Display 1500 may include a CHANGE STATUS TO section 1506. The CHANGE STATUS TO section 1506 may include options that enable the user to change the status of a new or existing action. In some embodiments, the options may include ASSIGNED, PENDING, or CLOSED.

Display 1500 may include a NOTES section 1508. In some embodiments, the NOTES section 1508 may be enabled only if in the CHANGE STATUS TO section 1506 has the option PENDING selected. The NOTES section 1508 may be used to enter an explanation as to why an action is PENDING. In some embodiments, the NOTES section 1508 may always be enabled and permit the user to add any notes regarding the case. The user may also review note history and enter a current note. The user can also return the case to a case manager (e.g., the patient evaluator manager 402) using the RETURN TO CASE MANAGER option 1510.

When the user is a manager of other users (e.g., the patient evaluator manager 402), the user may use display 1600 to assign cases to other users.

The display 1700 is an example display for polypharmacy. The display 1700 presents a graphical chart to the user of the amount of drug use by the member in the care coordination subsystem 502. The polypharmacy graphic 1700 may be displayed in the care coordination subsystem 502 in a separate tab or within one of the above-mentioned displays. The graphical chart 1700 may enable the user to determine the drug burden on the member and whether the user should consider a change in the medications used by the member.

The example polypharmacy information shown in display 1700 includes therapy classes, possible users, drugs, and a time period. The time period includes the quantity of drugs in the fill and the manner in which the drugs were filled (e.g., retail or mail order).

Figure 18:
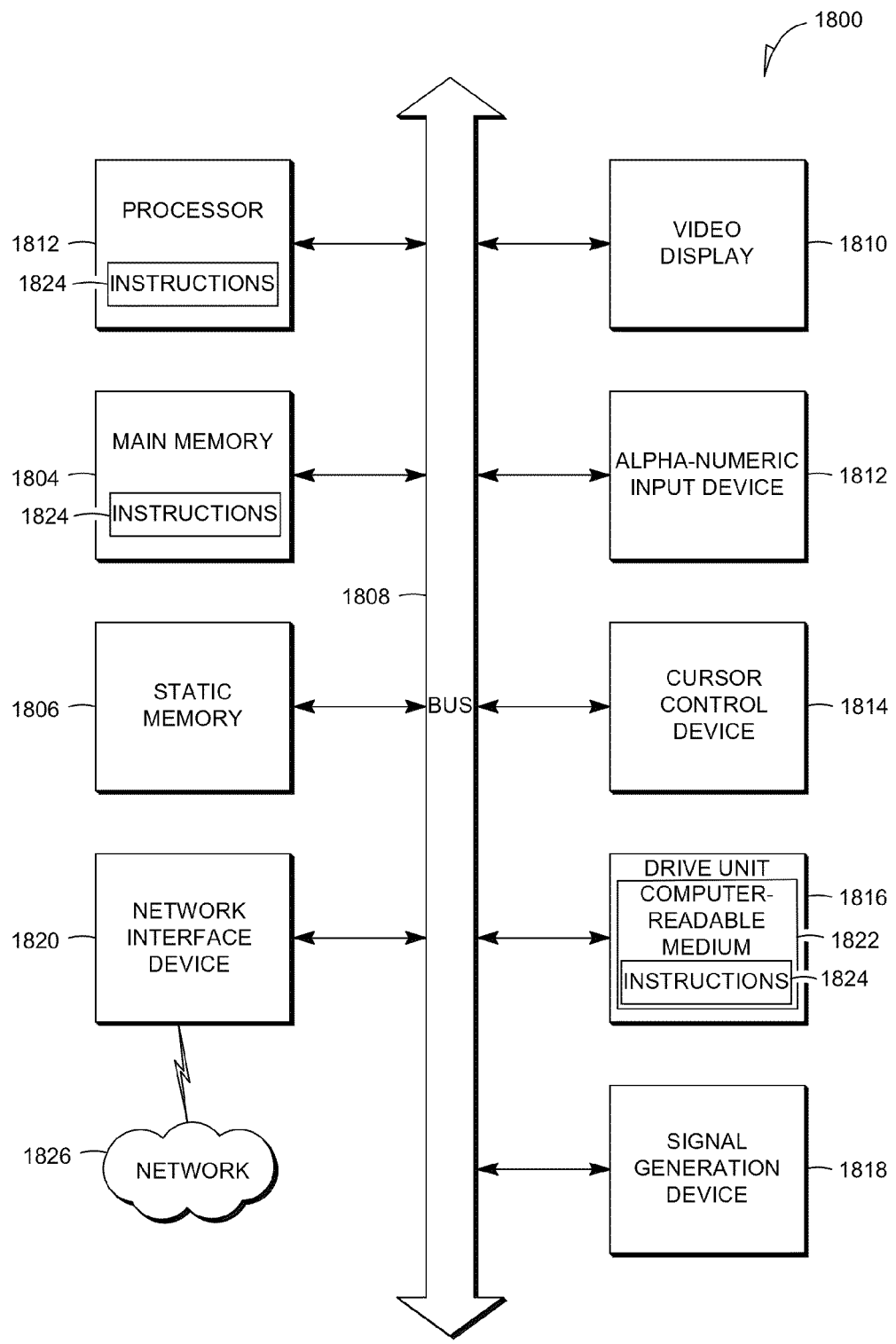
FIG. 18 is a block diagram of a machine in the example form of a computer system within which a set of instructions for causing the machine to perform any one or more of the methodologies discussed herein may be executed.

FIG. 18 shows a block diagram of a machine in the example form of a computer system 1800 within which a set of instructions may be executed causing the machine to perform any one or more of the methods, processes, operations, or methodologies discussed herein. The client device 102, the care coordination device 106, and/or the patient evaluator device 108 may include the functionality of the one or more computer systems 1800.

The disease management care coordination subsystem 502 may include tools to further facilitate communication and maximize best practices between organizations. In some embodiments, a workforce management function may be included. Individual targets supplied by the healthcare coordinator may be loaded into the disease management care coordination subsystem 502 for review by users (e.g., health management vendors, nurses, clients, health care professionals). The targets may be sorted using various clinical and operational filters. An example of a clinical filter may be sorting a target by disease state or age. An example of an operational filter may include monetary or pharmacy claims, thresholds or multiple concurrent cases. Both filters may be driven by an indicator that may be derived from the target data within the disease management care coordination subsystem 502. These may include slide filters and searches and assignment of cases.

In some embodiments, the ability to sort cases by Customer Defined Criteria called a Watch List may be included. Common methods to sort targeted members by the healthcare coordinator may include Member ID, Disease State, or by healthcare coordinator targets. Many healthcare management vendors (e.g., disease management vendors) may use both pharmacy and medical claims information in their choice to message a sick member. Other user may prefer to message members by location or use alternative criterion that may not be sortable using healthcare coordinator systems. The Watch list may be a cross reference file consisting of a healthcare coordinator identifier, a customer defined identifier, and a free text field that may be loaded into the health care coordinator system by the customer. As long as the healthcare coordinator identifier and at least one alternative field is populated, the system may assign these values to the healthcare coordinator targeting for viewing and sorting within the subsystem 502. This may permit the users in different organizations to continue to use their normal/desired processes of selecting members to message when evaluating the healthcare coordinator targets and improve efficiency and care coordination.

In some embodiments, polypharmacy and pill burden represented graphically. The polypharmacy graph may groups like drugs in therapy classes into categories and map fills by retail and mail order over a 120-day period. Visual representation of drug fills may enable users to identify wasteful polypharmacy and potential changes in therapy and gaps in care. A calculation for pill burden may be displayed either in or in conjunction with the polypharmacy graph to identify the severity of the polypharmacy.

The disease management care coordination subsystem 502 may provide features related to medical home. Medical home, which may also be known as the patient-centered medical home (PCMH) may be a health care setting that facilitates partnerships between individual members, their personal providers, and when appropriate, the family of the member. Medical home is an approach to providing comprehensive primary care to members. A medical home may associate the member with a core group of doctors or a doctor, rather than having the member visit multiple doctors for different symptoms. Medical home reduces the fractionalized care that may result from a member receiving care from multiple doctors who are not in coordination with each other. The medical home feature of the subsystem 502 may provide the healthcare provider with information for their member population. The healthcare provider may then identify a member and can identify whether the member is receiving care from another health care provider by accessing data associated with the member, such as claims information.

In some embodiments, the disease management care coordination subsystem 502 may include case tracking and reporting features. Users may have the ability to change the status of cases so the progress may be monitored from start to finish within the disease management care coordination subsystem 502. Closed cases, custom actions and notes entered by the user may be made available both in the case history of the member for later review as well as in summary and outcomes reporting. Additional reports using a multi-factorial method to evaluate member risk may be used and may be based on key pharmacy factors that contribute to pharmacy complications of a member. Drug spend, concurrent open healthcare coordinator cases, pill burden threshold (e.g., average pills consumed greater than ten per day) and predictive adherence risk scores for Hypertension, Diabetes and Cholesterol may be combined to create a total risk score. This report may enable users to identify member populations that require the most attention and care.

The disease management care coordination subsystem 502 may provide measurement tools for members. One example of a measurement tool is a medication possession ratio (MPR). The MPR uses the historical usage data of a particular drug and measures the percentage of time that a member took the medication. If the MPR falls below a certain threshold, the member may be categorized as non-adherent with the medication, which may identify that the member may be at risk. The care coordination subsystem 502 may generate several predictive model score for a member. The predictive model scores may be associated with drugs consumed by the member or disease states of the member. The predictive model scores may predict the potential future risk of the member. The different between a measurement tool, such as the MPR and the predictive model score is that the MPR is inherently a historical calculation, wherein the calculation is based upon historic data of the member. The predictive model score instead may use the claims history of the member and forecasts potential future risk for the member. Both types of tools may be displayed in the care coordination subsystem 502. By providing the predictive model score, which may be applied to various trigger data 122 of the member, the disease management care coordination subsystem 502 may provide the ability to quickly triage and prioritize members, to target members and track the progress of their actions throughout the disease management care coordination subsystem 502. The predictive model score may provide a more efficient way to address healthcare issues sooner.

Another measurement tool is pill burden. Pill burden is the number of pills that a member should consume in a day. In some cases, the higher the pill burden, the more likely members are to be non-adherent to their medication. A high pill burden may also lead to complications in drug interactions for the member and may reduce the effectiveness of the drug or give rise to unwanted side effects.

Combining the predictive modeling scores, triggers and measurements tools for open cases may enable users of the disease management care coordination subsystem 502 to evaluate members to assess their health risks. Using a variety of measurement tools and triggers may help users more efficiently triage and prioritize members and facilitate case management.

The disease management care coordination subsystem 502 may generate post-predictive model processing-aggregate scores for an individual using the output of the predictive modeling scores. In some embodiments, the disease management care coordination subsystem 502 may take all the predictive modeling scores associated with a member and manipulate the scores to generate a post-predictive model processing-aggregate score for a member. In some embodiments, the tool may take the median or the average of all the scores associated with the member. In some embodiments, the disease management care coordination subsystem 502 may take the average of a number of the lowest or highest values of the predictive modeling tools.

Responsive to generating the post-predictive model processing-aggregate scores for a member, the disease management care coordination subsystem 502 may display the score to a user of the system. The user may review the score and adjust the healthcare provided to the member based on the generated score. In some embodiments, the score may be used to target a certain population of the member population to prioritize high-risk members. In some embodiments, the score may be used to tailor the healthcare treatment being received by the member.

In some embodiments, the disease management care coordination subsystem 502 may provide security to safeguard patient health information, known in the industry as Protected Health Information. In some embodiments, lists may be created to restrict access to patient data, reports and functions at login. Members may be added or deleted to the lists by request to individuals with proper permissions. In some embodiments, the Protected Health Information of a patient may be managed by a different database or module.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1800 includes a processor 1812 (e.g., a central processing unit (CPU) a graphics processing unit (GPU) or both), a main memory 1804 and a static memory 1806, which communicate with each other via a bus 1808. The computer system 1800 may further include a video display unit 1180 (e.g., a liquid crystal display (LCD) or a cathode ray tube (CRT)). The computer system 1800 also includes an alphanumeric input device 1812 (e.g., a keyboard), a cursor control device 1814 (e.g., a mouse), a drive unit 1816, a signal generation device 1818 (e.g., a speaker) and a network interface device 1820.

The drive unit 1816 includes a computer-readable medium 1822 on which is stored one or more sets of instructions (e.g., software 1824) embodying any one or more of the methodologies or functions described herein. The software 1824 may also reside, completely or at least partially, within the main memory 1804 and/or within the processor 1812 during execution thereof by the computer system 1800, the main memory 1804 and the processor 1812 also constituting computer-readable media.

The software 1824 may further be transmitted or received over a network 1826 via the network interface device 1820.

While the computer-readable medium 1822 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In an example embodiment, a method for disease management care coordination may include integrating claim data associated with a prescription drug with additional health data from a plurality of data feeds received from a client device, a care coordination device, and a health management vendor device. The integrated data may be targeted to identify a member. The integrated data associated with the member maybe transmitted to a patient evaluator device. The integrated data may be updated using additional member information received from the patient evaluator device.

In an example embodiment, a non-transitory machine-readable medium comprising instructions, which when executed by one or more processors, may cause the one or more processors to perform the following operations: integrating claim data associated with a prescription drug with additional data from a plurality of data feeds received from a client device, a care coordination device, and a health management vendor device; targeting the integrated data to identify a member; transmitting the integrated data associated with the member to a patient evaluator device; and updating the integrated data using additional member information received from the patient evaluator device.

In an example embodiment, a system may include a processor; a memory coupled to the processor; an integration module deployed in the memory and executed by the processor to integrate claim data associated with a prescription drug with additional health data from a plurality of data feeds received from a client device, a care coordination device, and a health management vendor device; a targeting module deployed in the memory and executed by the processor to target the integrated data to identify a member; an integrated data transmission module deployed in the memory and executed by the processor to transmit the integrated data associated with the member to a patient evaluator device; and an integrated data update module deployed in the memory and executed by the processor to update the integrated data using additional member information received from the patient evaluator device.

In an example embodiment, targeting is run on the claims data using the targeting data. An evaluation request is received. A display may be generated based on running the targeting and receipt of the query request. Additional methods and systems are disclosed.

Thus, methods and systems for disease management care coordination have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method comprising:
storing, on a processor, an association of prescription drug claim data of a plan member of a pharmacy benefit plan with additional health data of the member from a plurality of data feeds received from a client device associated with a client of a pharmacy benefit manager, a care coordination device associated with a care coordinator that facilitates communication among a plurality of healthcare entities to address population pharmacy issues on behalf of the client, and a health management vendor device associated with a health management vendor to create integrated data associated with the member, the pharmacy benefit manager administering the pharmacy benefit plan for the member on behalf of the client;

accessing, on the processor, targeting data including a plurality of clinical-defined queries;

running, on the processor, the plurality of clinical-defined queries on the integrated data to identify a plurality of opportunity-available members as having an opportunity for clinical outreach;

determining, on the processor, for each of the plurality of opportunity-available members a prescription drug spend, a number of concurrent open healthcare coordinator cases, and a pill burden threshold;

calculating, on the processor, for each of the plurality of opportunity-available members a predicted adherence risk score for a disease state;

calculating, on the processor, a total risk score for each of the plurality of opportunity-available members based on the prescription drug spend, the number of concurrent open healthcare coordinator cases, the pill burden threshold, and the predicted adherence risk score for the disease state;

selecting, on the processor, a high risk member portion among the plurality of opportunity-available members based on the total risk score for each of the plurality of opportunity-available members;

transmitting, on the processor, the integrated data associated with the high risk member portion of the plurality of opportunity-available members to a patient evaluator device, the patient evaluator device associated with a patient evaluator;

updating, on the processor, the integrated data associated with the plan member using additional member information received from the patient evaluator device to create updated integrated data, the additional member information including documentation of clinical outreach performed on the member by the patient evaluator, the plan member being among the high risk member portion of the plurality of opportunity-available members; and generating, on the processor, a report based on the updated integrated data.

2. The method of claim 1, further comprising:
associating the member with a case designation based on identification of the member as having an opportunity for clinical outreach; and
assigning the case designation to the patient evaluator among a plurality of available patient evaluators.

3. The method of claim 2, further comprising:
receiving an evaluation request from the patient evaluator device, the evaluation request identifying the patient to be evaluated by the patient evaluator;
transmitting a patient profile to the patient evaluator device, the patient profile including trigger data and the integrated data associated with the member;
updating the patient profile using information received from the patient evaluator device; and
generating a response to the evaluation request based on updating the patient profile.

4. The method of claim 2, wherein assignment of the case designation is based on relative experience of the plurality of available patient evaluators, background of the plurality of available patient evaluators, case load of the plurality of available patient evaluators, or combinations thereof.

5. The method of claim 2, further comprising:
running the plurality of clinical-defined queries on the updated integrated data to identify the member as having an additional opportunity for clinical outreach;
transmitting the updated integrated data associated with the member to an additional patient evaluator device, the additional patient evaluator device associated with an additional patient evaluator that is different than the patient evaluator; and
further updating the updated integrated data associated with the member using further additional member information received from the additional patient evaluator device, the additional member information including documentation of the clinical outreach performed on the member by the additional patient evaluator.

6. The method of claim 5, wherein the patient evaluator is associated with clinical outreach for a first disease and the additional patient evaluator is associated with clinical outreach for a second disease state, the first disease state being a different disease state than the second disease state.

7. The method of claim 1, wherein the client associated with the client device is an employer group.

8. The method of claim 1, wherein the additional health data of the member includes demographic information of the member, claims information associated with the member, and historical target information identifying a past instance where the member has been targeted for patient evaluator care coordination.

9. The method of claim 1,
wherein the report is an operational level report including data from the plurality of data feeds associated with the member.

10. The method of claim 1,
wherein the report is a summary level report including data from the plurality of data feeds associated with a plurality of members, the plurality of members including the member.

11. The method of claim 1, further comprising:
providing a data feed of the updated integrated data.

12. The method of claim 1, wherein the additional health data includes lab results, clinical notes, notes associated with outcomes resulting from member interaction, data derived from member interaction, or combinations thereof.

13. The method of claim 1, wherein the additional health data includes medical claims data.

14. The method of claim 1, further comprising:
receiving the additional member information from the patient evaluator device,
wherein updating the integrated data is based on receipt of the additional member information.

15. The method of claim 14, wherein the additional member information received from the patient evaluator device includes information received by the patient evaluator device regarding a communication between the member and the patient evaluator.

16. The method of claim 15, wherein the communication between the member and the patient evaluator is associated with a particular aspect of the integrated data.

17. The method of claim 1, further comprising:
receiving the prescription drug claim data from the care coordination device.

18. The method of claim 1, further comprising:
receiving the prescription drug claim data from an additional care coordination device, the additional care coordination device being a different device than the care coordination device.

19. The method of claim 1, wherein a member population of the client includes the plurality of opportunity-available members and a plurality of additional members.

20. The method of claim 1, wherein a clinical-defined query of the plurality of clinical-defined queries includes patient-inclusive criteria, patient-exclusive criteria, or both patient-inclusive criteria and patient-exclusive criteria for member identification.

21. The method of claim 1, wherein running the plurality of clinical-defined queries on the integrated data associated with the member identifies a plurality of members having an opportunity for clinical outreach, the plurality of members including the member, wherein transmitting the integrated data associated with the member includes transmitting the integrated data associated with the plurality of members to the patient evaluator device, the method further comprising:

receiving member identification of the member from the patient evaluator device, wherein updating the integrated data associated with the member is based on receipt of the member identification.

22. The method of claim 1, wherein the plurality of clinical-defined queries include a plurality of predefined-clinical queries.

23. A non-transitory machine-readable medium comprising instructions, which when executed by one or more processors, cause the one or more processors to perform the following operations:

store an association of prescription drug claim data a of a member of a pharmacy benefit plan with additional health data of the member from a plurality of data feeds received from a client device associated with a client of a pharmacy benefit manager, a care coordination device associated with a care coordinator that facilitates communication among a plurality of healthcare entities to address member population pharmacy issues on behalf of the client, and a health management vendor device associated with a health management vendor to create integrated data associated with the member, the pharmacy benefit manager administering the pharmacy benefit plan for the member on behalf of the client;

access targeting data including a plurality of clinical-defined queries;

run the plurality of clinical-defined queries on the integrated data to identify a plurality of opportunity-available members as having an opportunity for clinical outreach;

determine for each of the plurality of opportunity-available members a prescription drug spend, a number of concurrent open healthcare coordinator cases, and a pill burden threshold;

calculate for each of the plurality of opportunity-available members a predicted adherence risk score for a disease state;

calculate a total risk score for each of the plurality of opportunity-available members based on the prescription drug spend, the number of concurrent open healthcare coordinator cases, the pill burden threshold, and the predicted adherence risk score for the disease state;

select a high risk member portion among the plurality of opportunity-available members based on the total risk score for the plurality of opportunity-available members;

transmit the integrated data associated with the high risk member portion of the plurality of opportunity-available members to a patient evaluator device, the patient evaluator device associated with a patient evaluator; and update the integrated data associated with the member using additional member information received from the patient evaluator device to create updated integrated data, the additional member information including documentation of clinical outreach performed on the member by the patient evaluator, the member being among the high risk member portion of the plurality of opportunity-available members; and generate a report based on the updated integrated data.

24. The non-transitory machine-readable medium of claim 23, wherein the instructions are further executed by the one or more processors to associate the member with a case designation based on identification of the member as having an opportunity for clinical outreach; and assign the case designation to the patient evaluator among a plurality of available patient evaluators.

25. The non-transitory machine-readable medium of claim 24, wherein the instructions are further executed by the one or more processors to receive an evaluation request from the patient evaluator device, the evaluation request identifying the patient to be evaluated by the patient evaluator;

transmit a patient profile to the patient evaluator device, wherein the patient profile includes trigger data and the integrated data associated with the member;

update the patient profile using information received from the patient evaluator device; and generate a response to the evaluation request based on updating the patient profile.

26. The non-transitory machine-readable medium of claim 23, wherein the instructions are further executed by the one or more processors to receive the additional member information from the patient evaluator device, wherein updating the integrated data is based on receipt of the additional member information.

27. The non-transitory machine-readable medium of claim 23, wherein the instructions are further executed by the one or more processors to receive the prescription drug claim data from the care coordination device.

28. The non-transitory machine-readable medium of claim 23, wherein the instructions are further executed by the one or more processors to receive the prescription drug claim data from an additional care coordination device, the additional care coordination device being a different device than the care coordination device.

29. A system comprising:

a processor and a memory coupled to the processor;

an integration module deployed in the memory and executed by the processor to storing an association of prescription drug claim data of a member of a pharmacy benefit plan with additional health data of the member from a plurality of data feeds received from a client device associated with a client of a pharmacy benefit manager, a care coordination device associated with a care coordinator that facilitates communication among a plurality of healthcare entities to address member population pharmacy issues on behalf of the client, and a health management vendor device associated with a health management vendor to create integrated data associated with the member, the pharmacy benefit manager administering the pharmacy benefit plan for the member on behalf of the client;

a targeting module deployed in the memory and executed by the processor to access targeting data including a plurality of clinical-defined queries and run the plurality of clinical-defined queries on the integrated data to identify a plurality of opportunity-available members as having an opportunity for clinical outreach;

an integrated data transmission module deployed in the memory and executed by the processor to transmit the integrated data associated with the high risk member portion of the plurality of opportunity-available members to a patient evaluator device, the patient evaluator device associated with a patient evaluator;

an allocation module deployed in the memory and executed by the processor to determine for each of the plurality of opportunity-available members a prescription drug spend, a number of concurrent open healthcare coordinator cases, and a pill burden threshold, calculate for each of the plurality of opportunity-available members a predicted adherence risk score for a disease state, calculate a total risk score for each of the plurality of opportunity-available members based on the prescription drug spend, the number of concurrent open healthcare coordinator cases, the pill burden threshold, and the predicted adherence risk score for the disease state, and select a high risk member portion among the plurality of opportunity-available members based on the total risk score for the plurality of opportunity-available members;

an integrated data update module deployed in the memory and executed by the processor to update the integrated data associated with the member using additional member information received from the patient evaluator device to create updated integrated data, the additional member information including documentation of clinical outreach performed on the member by the patient evaluator, the member being among the high risk member portion of the plurality of opportunity-available members; and a reporting module deployed in the memory and executed by the processor to generate a report based on the updated integrated data.

30. The system of claim 29, further comprising:

an allocation module deployed in the memory and executed by the processor to associate the member with a case designation based on identification of the member as having an opportunity for clinical outreach; and a tracking module deployed in the memory and executed by the processor to assign the case designation to the patient evaluator among a plurality of available patient evaluators.

31. The system of claim 30, further comprising:

a request receiver module deployed in the memory and executed by the processor to receive an evaluation request from the patient evaluator, the evaluation request identifying the patient to be evaluated by the patient evaluator;

a transmission module deployed in the memory and executed by the processor to transmit a patient profile to the patient evaluator device, the patient profile includes trigger data and the integrated data associated with the member; and the integrated data update module deployed in the memory and executed by the processor to update the patient profile using information received from the patient evaluator device;

wherein the request receiver module is configured to generate a response to the evaluation request based on updating the patient profile.

32. The system of claim 29, wherein the integration module is further configured to receive the additional member information from the patient evaluator device, wherein updating the integrated data is based on receipt of the additional member information.

33. The system of claim 29, wherein the integration module is further configured to receive the prescription drug claim data from the care coordination device.

34. The system of claim 29, wherein the integration module to receive the prescription drug claim data from an additional care coordination device, the additional care coordination device being a different device than the care coordination device.

* * * * *